(12) United States Patent
Hampson et al.

(10) Patent No.: US 11,738,024 B2
(45) Date of Patent: Aug. 29, 2023

(54) LOPINAVIR AND RITONAVIR FOR THE TREATMENT OF CERVIX DISORDERS

(71) Applicant: DOUGLAS PHARMACEUTICALS LIMITED, Auckland (NZ)

(72) Inventors: Ian Hampson, Manchester (GB); Lynne Hampson, Manchester (GB)

(73) Assignee: Douglas Pharmaceuticals Limited, Lincoln (NZ)

( * ) Notice: Subject to any disclaimer, the term of this patent is extended or adjusted under 35 U.S.C. 154(b) by 0 days.

(21) Appl. No.: 17/055,048

(22) PCT Filed: May 23, 2019

(86) PCT No.: PCT/IB2019/054292
§ 371 (c)(1),
(2) Date: Nov. 12, 2020

(87) PCT Pub. No.: WO2019/224779
PCT Pub. Date: Nov. 28, 2019

(65) Prior Publication Data
US 2021/0213015 A1    Jul. 15, 2021

(30) Foreign Application Priority Data
May 24, 2018 (GB) ..................... 1808564

(51) Int. Cl.
*A61K 31/513* (2006.01)
*A61P 15/02* (2006.01)
(Continued)

(52) U.S. Cl.
CPC .......... *A61K 31/513* (2013.01); *A61K 9/0034* (2013.01); *A61K 9/06* (2013.01);
(Continued)

(58) Field of Classification Search
CPC ...... A61K 31/513; A61K 9/0034; A61K 9/06; A61K 47/38
See application file for complete search history.

(56) References Cited

U.S. PATENT DOCUMENTS 9,782,409 B2  10/2017  Hampson et al.
10,251,884 B2  4/2019  Hampson et al.
(Continued)

FOREIGN PATENT DOCUMENTS

EP   0366277 A2   5/1990
EP   2613766 A2   7/2013
(Continued)

OTHER PUBLICATIONS

Remington Pharmaceutical Science, 19th Ed, 1995, pp. 1380, 1397-1404 (Year: 1995).*
(Continued)

*Primary Examiner* — San Ming R Hui
(74) *Attorney, Agent, or Firm* — Nixon Peabody LLP; Linda B. Huber

(57) ABSTRACT

The present invention concerns pharmaceutical compositions formulated for topical application that are useful in the treatment of HPV-related pathologies and in particular the treatment of premalignant and malignant conditions of the cervix. The com-positions comprise a therapeutically effective amount of lopinavir and ritonavir in a pharmaceutically acceptable vehicle and wherein the weight ratio (w/w) of lopinavir: ritonavir is between 9:1 and 18:1.

18 Claims, 9 Drawing Sheets

(51) Int. Cl.
A61K 9/00 (2006.01)
A61K 9/06 (2006.01)
A61K 31/427 (2006.01)
A61K 47/38 (2006.01)

(52) U.S. Cl.
CPC ............ *A61K 31/427* (2013.01); *A61K 47/38* (2013.01); *A61P 15/02* (2018.01)

(56) References Cited

U.S. PATENT DOCUMENTS

| | | |
|---|---|---|
| 2002/0198160 A1 | 12/2002 | Everitt et al. |
| 2003/0129208 A1 | 7/2003 | Alberts et al. |
| 2005/0143404 A1 | 6/2005 | Rosenberg et al. |
| 2010/0173861 A1 | 7/2010 | Huang et al. |
| 2012/0219602 A1 | 8/2012 | Flack et al. |
| 2016/0271132 A1 | 9/2016 | Hampson et al. |
| 2018/0161328 A1 | 6/2018 | Hampson et al. |
| 2021/0213016 A1 | 7/2021 | Hampson et al. |
| 2022/0257771 A1 | 8/2022 | Hampson et al. |

FOREIGN PATENT DOCUMENTS

| | | | |
|---|---|---|---|
| EP | 3603637 A1 | 2/2020 | |
| WO | 200152821 A1 | 7/2001 | |
| WO | 2004010937 A2 | 2/2004 | |
| WO | 2005007070 A2 | 1/2005 | |
| WO | 2005053694 A1 | 6/2005 | |
| WO | 2011128623 A2 | 10/2011 | |
| WO | 2013034927 A1 | 3/2013 | |
| WO | 2015059485 A1 | 4/2015 | |
| WO | WO-2015059485 A1 * | 4/2015 | ........... A61K 31/427 |
| WO | 2016123541 A1 | 8/2016 | |
| WO | 2019130341 A1 | 7/2019 | |
| WO | 2019224776 A1 | 11/2019 | |
| WO | 2019224777 A1 | 11/2019 | |
| WO | 2019224779 A1 | 11/2019 | |
| WO | 2019224780 A1 | 11/2019 | |
| WO | 2020234800 A1 | 11/2020 | |
| WO | 2021105922 A1 | 6/2021 | |

OTHER PUBLICATIONS

PCT/GB2014/053169 International Search Report and Written Opinion dated Jan. 28, 2015, 11 pages.
PCT/IB2019/054292 International Search Report and Written Opinion dated Sep. 17, 2019, 10 pages.
GB Search Report for GB1808563.9 dated Nov. 23, 2018, 2 pages.
PCT/IB2019/054293 International Search Report and Written Opinion dated Sep. 5, 2019, 8 pages.
Anonymous, Kaletra Cream Attacks HPV, May Stop Cervical Cancer, 2006, retrieved from: http://www.natap.org/2006HIV/082506_02.htm on Jan. 19, 2015, 3 pages.
Batman et al., Lopinavir Up-Regulates Expression of the Antiviral Protein Ribonuclease L in Human Papillomavirus-Positive Cervical Carcinoma Cells, Antiviral Therapy, 2011, vol. 16, pp. 515-525.
Zehbe et al., Lopinavir Shows Greater Specificity than Zinc Finger Ejecting Compounds as a Potential Treatment for Human Papillomavirus-Related Lesions, Antiviral Research, 2011, vol. 91, pp. 161-166.
Mo et al., Characterization of resistant HIV variants generated by in vitro passage with lopinavir/ritonavir, Antiviral Research, 2003, vol. 59(3).
Hampson et al., A Single-Arm, Proof-Of-Concept Trial of Lopimune (Lopinavir/Ritonavir) as a Treatment of HPV-Related Pre-Invasive Cervical Disease, PLOS One, 2016, vol. 11(1).
GlitterGalore, 2017, Lopinavir/ritonavir as a topical cream for HPV, CancerCompass, retrieved from: https://www.cancercompass.com/message-board/message/all,133989,0.htm.
International Search Report and Written Opinion for PCT/IB2020/054787 dated Nov. 13, 2020, 19 pages.
Soren Gantt et al., The HIV Protease Inhibitor Nelfinavir Inhibits Kaposi's Sarcoma-Associated Herpesvirus Replication In Vitro, Antimicrobial Agents and Chemotherapy, 2011, vol. 55(6), pp. 2696-2703.
Harmenberg et al., Prevention of ulcerative lesions by episodic treatment of recurrent herpes labialis: A literature review, Acta Derm Venereol, 2010, vol. 90(2), pp. 122-130.
Piret et al., Antiviral resistance in herpes simplex virus and varicella-zoster virus infections: Diagnosis and management, Current Opinion in Infectious Diseases, 2016, vol. 29(6), pp. 654-662.
Katsumata et al., Antiviral efficacy of the helicase-primase inhibitor amenamevir in murine models of severe herpesvirus infection, Biochemical Pharmacology, 2018, vol. 158(1), pp. 201-206.
Kalu et al., Nelfinavir Inhibits Maturation and Export of Herpes Simples Virus 1, Journal of Virology, 2014, vol. 88(10), pp. 5455-5461.
Slyker et al., Acclerated Suppression of Primary Epstein-Barr Virus Infection in HIV-Infected Infants Initating Lopinavir/ Ritonavir-Based Versus Nevirapine-Based Combination Antiretroviral Therapy, Clinical Infection Diseases, 2014, vol. 68(9), pp. 1333-1337
Liu et al., Bowman-Birk inhibitor suppresses herpes simplex virus type 2 infection of human cervical epithelial cells, Viruses, 2018, vol. 10(557), pp. 1-17
Gantt et al., Nelfinavir Impairs Glycosylation of Herpes Simplex Virus 1 Envelope Proteins and Blocks Virus Maturation, Advances in Virology, 2015, pp. 1-9
Exam Report for EP 19732473.4 dated Feb. 15, 2023, 3 pages
International Search Report and Written Opinion for PCT/IB2020/061183, dated Mar. 10, 2021, 10 pages.
EPO Exam Report for EP 20760530.4 dated Jan. 18, 2023, 7 pages
UK Search Report for GB 1917252.7 dated May 22, 2020, 2 pages

* cited by examiner

Hela Cell 20µM 11.0 - 13.5 : 1 Lopinavir/Ritonavir Ratios

LOPINAVIR AND RITONAVIR FOR THE TREATMENT OF CERVIX DISORDERS

CROSS-REFERENCE TO RELATED APPLICATIONS

This application is a National Phase of International Application No. PCT/IB2019/054292, filed May 23, 2019, which designated the U.S. and that International Application was published under PCT Article 21(2) in English. This application also includes a claim of priority under 35 U.S.C. § 119(a) and § 365(b) to British patent application No. GB 1808564.7, filed May 24, 2018, the contents of which are herein incorporated by reference in their entirety.

Provided herein are methods and compositions for treating and/or inhibiting the development or progression of cancers and benign proliferative disorders of the cervix and particularly such cancers and disorders caused by human tumour viruses such as human papilloma virus (HPV). In particular compositions are provided comprising lopinavir and ritonavir for use in treating and/or inhibiting the progression of HPV related dysplasia of the cervix.

BACKGROUND

Many different forms of cancer exist, and it is believed that there are many different causes of the disease. The incidence of cancer varies, but it represents the second highest cause of mortality, after heart disease, in most developed countries. Current estimates suggest that one in three Americans alive at present will suffer from some form of cancer. There is a well-recognised need to develop new and improved therapies for treating cancers. Furthermore, there is also a requirement to develop therapeutic agents that may be used to inhibit the development of cancer in the general population, susceptible high-risk individuals or as an agent to prevent re-occurrence of disease in individuals already affected.

Human tumour viruses are recognised to be a major cause of human cancer, and there is a great deal of evidence which supports the contention that these viruses cause cancer by inducing genetic instability in infected cells. Indeed, both the human T-cell leukaemia virus type 1 (HTLV1) Tax and the human papilloma virus type 16 (HPV16) E6 oncoproteins are known to induce genetic instability producing abnormal numbers of centrosomes, multinucleation and nuclear atypia.

Invasive cervical cancer (ICC) is an example of a cancer associated with viral infection which causes >270,000 deaths per annum with over 85% of these occurring in low resource countries. Infection with high-risk types of HPV has been established as the main aetiological agent for ICC. The development of ICC can take 10-20 years and is preceded by HPV related pre-invasive pathology which is characterised as either low-grade (CIN1) or high-grade cervical intraepithelial neoplasia (CIN2/3). Lesions can be screened for by cervical cytology testing where they are diagnosed (or graded) as either borderline atypical squamous cells of undetermined significance (ASCUS), low-grade squamous intraepithelial lesions (LSIL) or high-grade squamous intraepithelial lesions (HSIL).

The reduction in ICC related mortality in the developed world has been largely dependent on organised cytology screening and similar trends in cervical cancer mortality have been achieved by organised single screen and treatment in the rest of the world. However, in the poorer nations lack of resources and health education means that most pre-invasive cervical disease remains undiagnosed and untreated. Thus, where resources are limited, low-cost screening and treatment options are clearly a high priority.

Current treatment options in clinical practice are either by ablative (destructive) or excisional modalities. Systematic reviews have demonstrated that these treatment modalities have similar success rates but have different morbidities. In the developed world, Large Loop Excision of the Transformation Zone LLETZ (aka loop electrosurgical excision procedure—LEEP) is used in most colposcopy clinics. Over 80% of these procedures are performed under local analgesia and the whole of the transformation zone is available for subsequent histological examination. The procedure is associated with a risk of primary/secondary haemorrhage, prolonged discharge, infection and a risk of preterm delivery in subsequent pregnancies. The former side effects can be problematic particularly in low resource countries. Ablative treatment in the form of cold coagulation and cryotherapy are often advocated for use in low resource countries since these are low cost, require minimal infrastructure and can be carried out by trained non-medical health professionals. However, some studies have suggested that cryotherapy has a higher failure rate compared to other treatment modalities.

There are a variety of locally-applied, non-surgical approaches which have been evaluated for the treatment of cervical dysplasia including; photodynamic therapy (PDT); off-licence use of the anti-cytomegalovirus (CMV) drug cidofovir; local application of the immune activator Imiquimod and direct application of the cytotoxic drug 5 flurouracil (5FU). Although some of these alternative treatment modalities show promise, their treatment outcomes are inferior to the reported 80-95% success rates obtained in quality assured colposcopy units.

An effective, inexpensive, non-surgical, self-applied treatment for HPV related cervical dysplasia would have great potential particularly in low resource settings. Furthermore, improved compliance with topical treatment would be enhanced, if the side effects are minimised.

A recent advance in the treatment of cancers caused by viruses is disclosed in WO2015/059485 which describes the protease inhibitors, lopinavir and ritonavir (which had previously been used as orally ingested medicaments for the clinical management of retroviral infections such as HIV) as being clinically useful for topical administration to tissues to prevent or treat malignancies caused by HPV. The authors were particularly surprised to find that soft capsules of KALETRA® (which were marketed by Abbott/Abbvie for the treatment of HIV infections by oral administration) can be administered topically (i.e. inserted into the vagina for treatment of the cervix) for the prevention or treatment of cancerous conditions, for the prevention or treatment of oncogenic viral infections and for the prevention or treatment of benign proliferative orders.

KALETRA® (or its equivalent LOPIMUNE) is available for oral consumption as a solution comprising 80 mg lopinavir and 20 mg ritonavir per millilitre or as a soft capsule for oral administration that comprises 133.3 mg lopinavir and 33.3 mg ritonavir. In both cases the active pharmaceutical ingredients (APIs) are present in a ratio of 4:1 (lopinavir:ritonavir). Given that the authors of WO2015/059485 found soft capsules of KALETRA® to be efficacious, they reasoned that a ratio of 4:1 would be optimal for topical use.

The present invention is based on work carried out by the inventors to formulate a bespoke formulation of lopinavir and ritonavir for topical application. They have unexpectedly established that the ratio of APIs found in known pharmaceutical products comprising lopinavir and ritonavir (e.g. LOPIMUNE or KALETRA®) may have efficacy, but are not optimal for treating and/or inhibiting the development or progression of cancers and benign proliferative disorders of the cervix and the present invention provides compositions comprising optimal ratios of lopinavir:ritonavir for use in treating and/or inhibiting the development of such conditions.

SUMMARY

Disclosed herein are compositions comprising lopinavir in combination with ritonavir for use as a medicament in the treatment of cervical cancer or benign proliferative disorders of the cervix or in the prevention of the development of such cancers and disorders.

According to a first aspect of the invention there is provided a pharmaceutical composition that is formulated for topical application comprising a therapeutically effective amount of lopinavir and ritonavir in a pharmaceutically acceptable vehicle wherein the weight (w/w) ratio of lopinavir: ritonavir is between 9:1 and 18:1.

According to a second aspect of the invention there is provided a pharmaceutical composition according to the first aspect of the invention for use as a medicament in treating and/or inhibiting the development or progression of cervical cancers and benign proliferative disorders of the cervix.

According to a third aspect of the invention there is provide a method of treating and/or inhibiting the development or progression of cervical cancers and benign proliferative disorders of the cervix in a subject in need of such treatment or inhibition comprising administering a therapeutically effective amount of a pharmaceutical composition according to the first aspect of the invention to said subject.

It is preferred that the cancer or benign proliferative disorder is caused by a viral infection, more preferably by an oncogenic virus and, in particular, human tumour viruses such as HPV.

In a preferred embodiment the invention concerns treating a subject having an HPV related dysplasia of the cervix comprising administering to said subject a therapeutically effective dose of the disclosed pharmaceutical compositions.

BRIEF DESCRIPTION OF THE DRAWINGS

The summary, as well as the following detailed description, is further understood when read in conjunction with the appended drawings. For the purposes of illustrating the disclosed compositions and methods, there are shown in the drawings exemplary embodiments of the compositions and methods; however, the compositions and methods are not limited to the specific embodiments disclosed. In the drawings.

DETAILED DESCRIPTION

Figure 1:
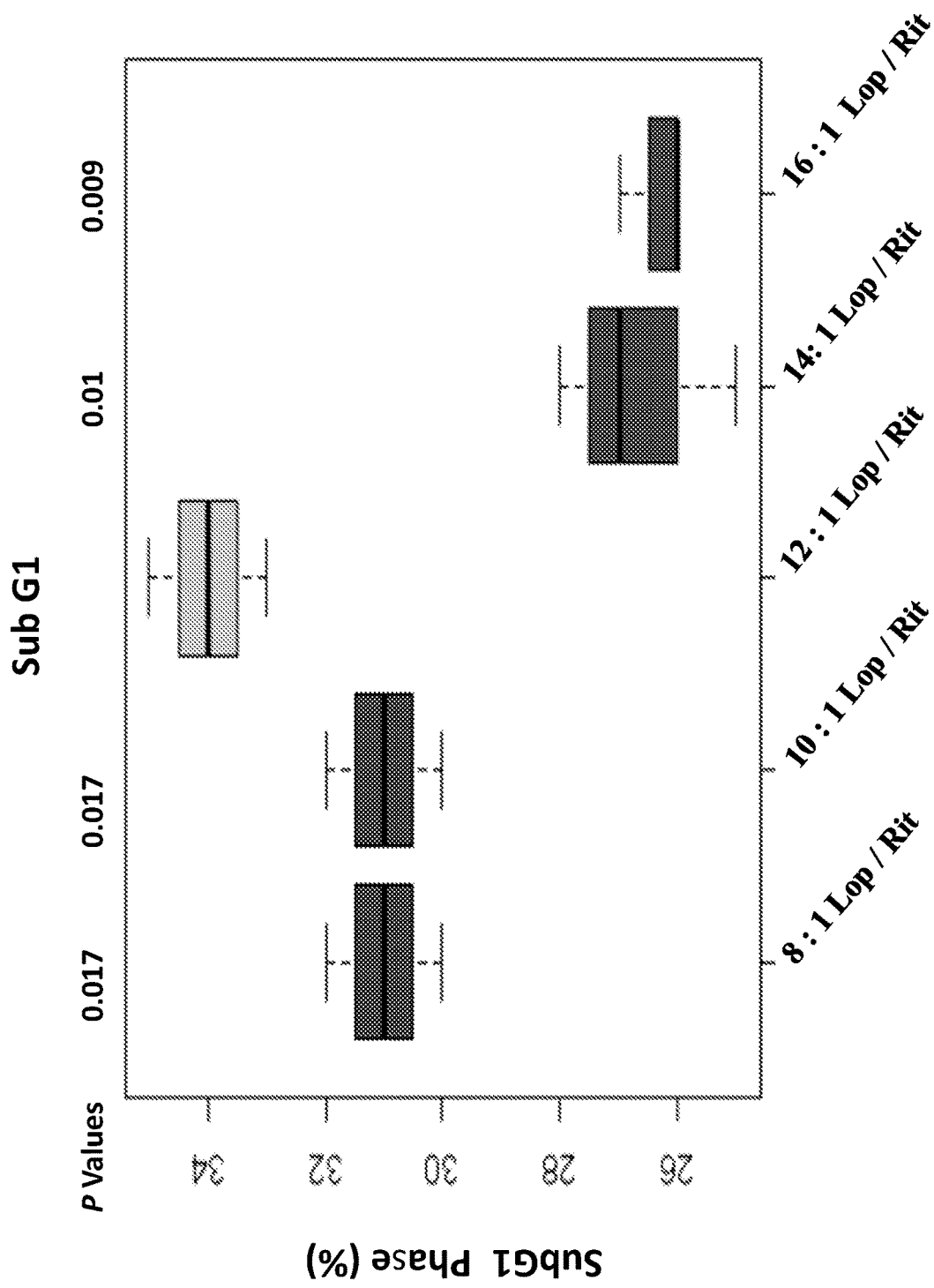
FIG. 1 represents a bar chart illustrating the effects of various weight ratios of lopinavir:ritonavir on inducing apoptosis in E6/E7 immortalised non-transformed endocervical cells as discussed in Example 1.

The disclosed compositions and methods may be understood more readily by reference to the following detailed description taken in connection with the accompanying figures, which form a part of this disclosure. It is to be understood that the disclosed compositions and methods are not limited to the specific compositions and methods described and/or shown herein, and that the terminology used herein is for the purpose of describing particular embodiments by way of example only and is not intended to be limiting of the claimed compositions and methods.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

It is to be appreciated that certain features of the disclosed compositions and methods which are, for clarity, described herein in the context of separate embodiments, may also be provided in combination in a single embodiment. Conversely, various features of the disclosed compositions and methods that are, for brevity, described in the context of a single embodiment, may also be provided separately or in any subcombination.

As used herein, the singular forms "a," "an," and "the" include the plural.

The following abbreviations are used herein: human papilloma virus (HPV); Atypical squamous cells of undetermined significance (ASC-US); Low grade squamous intraepithelial lesion (LSIL); Atypical squamous cells—cannot exclude HSIL (ASC-H); High grade squamous intraepithelial lesion (HSIL); Squamous cell carcinoma (SCC); Abnormal glandular cells (AGC); Cervical intraepithelial neoplasia 1 (CIN1); Cervical Intraepithelial neoplasia 2 (CIN2); Cervical intraepithelial neoplasia 3 (CIN3); Carcinoma in situ (CIS); Invasive Cervical Carcinoma (ICC).

When values are expressed as approximations, by use of the antecedent "about," it will be understood that the particular value forms another embodiment. Furthermore, the term "about" when used in reference to numerical ranges, cut-offs, or specific values is used to indicate that the recited values may vary by up to as much as 10% from the listed value. As many of the numerical values used herein are experimentally determined, it should be understood by those skilled in the art that such determinations can, and often will, vary among different experiments. The values used herein should not be considered unduly limiting by virtue of this inherent variation. Thus, the term "about" is used to encompass variations of ±10% or less, variations of ±5% or less, variations of ±1% or less, variations of ±0.5% or less, or variations of ±0.1% or less from the specified value.

As used herein, "treating" and like terms refer to reducing the severity and/or frequency of symptoms, eliminating symptoms and/or the underlying cause of said symptoms, reducing the frequency or likelihood of symptoms and/or their underlying cause, delaying, preventing and/or slowing the progression cancers or benign proliferative disorders, and improving or remediating damage caused, directly or indirectly, by the cancers or disorders.

As used herein, the phrase "therapeutically effective dose" refers to an amount of a composition comprising lopinavir and ritonavir, as described herein, effective to achieve a particular biological or therapeutic result such as, but not limited to, biological or therapeutic results disclosed, described, or exemplified herein. The therapeutically effective dose may vary according to factors such as the disease state, age, sex, and weight of the individual, and the ability of the composition to cause a desired response in a subject. Such results include, but are not limited to, the reduction, remission, and/or regression of the benign or malignant disease or prevention of the development of the benign or malignant disease, as determined by any means suitable in the art.

As used herein, "subject" includes a vertebrate, mammal, domestic animal or preferably a human being.

The "pharmaceutically acceptable vehicle" may be any physiological vehicle known to those of ordinary skill in the art useful in formulating pharmaceutical compositions. The vehicle is most suitably one suited for delivery of the Active Pharmaceutial Ingredients (APIs) to a target tissue by topical application.

As used herein, "ovule" refers to a cream or gel containing solid or semi-solid suppository configured for insertion into the vagina.

Disclosed herein are compositions comprising lopinavir and ritonavir for use as a medicament in the treatment of cervical cancer or benign proliferative disorders of the cervix (e.g. warts) or in the prevention of the development of cervical cancer.

Lopinavir (CAS# 192725-17-0) is a protease inhibitor chemically designated as [1S-[[1R*(R*), 3R*, 4R*]]-N[4-[(2,6-dimethylphenoxy0acetyl]amino]-3-hydroxy-5-phenyl-1-(phenylmethyl)pentyl]tetrahydro-alpha-(1-methylethyl)-2-oxo-1(2H)-pyrimidineacetamide. It has the molecular formula C37H48N4O5 and a molecular weight of 628.80.

Ritonavir (CAS# 155214-67-5) is a protease inhibitor chemically designated as 10-Hydroxy-2-methyl-5-(1-methylethl)-1-[2-(1-methylethyl)-4-thiazolyl]-3,6-dioxo-8,11bis(phenylmethyl)-2,4,7,12-tetraazatridecan-13-oic acid, 5-thiazolylmethylester, [5S-(5R*,8R*,10R8,11R*)]. It has the molecular formula $C_{37}H_{48}N_6O_5S_2$ and a molecular weight of 720.95.

Surprisingly, in view of the prior art, the inventors have found that molar ratios of lopinavir:ritonavir for treating, or preventing the development of, cervical cancer or benign proliferative disorders of the cervix or for prevention of the development of such cancers or such disorders should optimally be in the molar ratio range of 10:1-18:1. The range may be 10.5:1-18:1. Preferably the range is 11.5:1-17:1, more preferably 11.5:1-16.0:1 and even more preferably 11.5:1-15:1 The range may be a molar ratio of about 11.75: 1; about 12:1; about 12.5:1; about 13:1; about 13.5:1; about 13.75:1; about 14.0:1; or about 14.5:1. In a preferred embodiment the molar ratio of lopinavir:ritonavir is about 12:1. In another preferred embodiment the molar ratio of lopinavir:ritonavir is about 13.8:1.

In a preferred embodiment the molar ratio of Lopinavir:ritonavir is between 11:1 and 16:1, more preferably between 11:1 and 13:5 and most preferably between 11:1 and 12.5:1. Most preferred molar ratios are 11:1, 11.5:1 and 12:1.

It will be appreciated that lopinavir has a molecular weight of 628.8 daltons and ritonavir has a molecular weight of 720.95 daltons. Accordingly molar ratios and w/w ratios will not be the same and a factor of 0.872 should be applied when converting molar ratios to w/w. Accordingly the inventors have found that w/w ratios of lopinavir:ritonavir for treating, or preventing the development, of cervical cancer or benign proliferative disorders of the cervix or for prevention of the development of such cancers or such disorders may be in the weight ratio range 9:1-18:1 or 9:1-16:1. For instance the range may be 9.5:1-16:1 or 10.0:1-16:1. Preferably the range is 10.0:1-15.0:1, more preferably 10.25:1-14.5:1 and most preferably 10.5:1-13.0:1. The range may be a w/w ratio of about 10.25: 1; about 10.5:1; about 10.75:1; about 11:1; about 11.25:1; about 11.5:1; about 11.75:1; about 12.0:1; about 12.25:1; about 12.5:1; about 12.75: about 13.0:1; about 13.25:1; about 13.5:1; about 13.75:1; about 14.0:1 or about 14:25:1. In a preferred embodiment the w/w ratio of lopinavir:ritonavir is about 10.5:1. In a most preferred embodiment the w/w ratio of lopinavir:ritonavir is about 12:1.

The compositions according to the first aspect of the invention are useful in the treatment of cervical cancer and particularly useful for preventing the development of such cancers. Accordingly, normal subjects (i.e. subjects with no detectable cancer), subjects with pre-malignant cells or particularly cancer prone subjects may be treated by topical administration of compositions according to the invention with a view to preventing the development of cervical cancer.

The invention is applicable particularly, but by no means exclusively, to pre-cancerous conditions of the cervix and cervical cancers caused by oncogenic viruses, e.g. high-risk or even low-risk forms of human papilloma viruses (HPVs).

According to a preferred embodiment of the invention, the compositions may be administered to treat, and particularly prevent, the development of cervical cancer. It is most preferred that the inhibitors are used to treat or prevent the development of cervical cancers caused by HPV (particularly high-risk types of HPV such as HPV16 or HPV 18).

In the developed nations that have cervical screening programs, HPV testing and cervical cytology are currently in a state of flux. At present, the cervical smear (or Pap test) is usually carried out prior to HPV testing with follow on procedures depending on the results obtained. However, depending on geographical location the HPV test may be given first. Table 1 shows a typical recommended management protocol based on the combined results of HPV and Pap tests.

TABLE 1

Recommended Management of combined HPV and Pap tests

| HPV test | Pap test | Management |
| --- | --- | --- |
| Negative | Negative | Repeat testing in 5 years |
| Any | Negative | Repeat testing in 3 years |
| Negative | ASC-US | Repeat testing in 3 years |
| Negative | LSIL | Repeat testing in 6-12 months |
| Not performed | ASC-US | Repeat testing in 6-12 months |
| Positive | Negative | Repeat testing in 6-12 months |

TABLE 1-continued

Recommended Management of combined HPV and Pap tests

| HPV test | Pap test | Management |
|---|---|---|
| Not performed | LSIL | Immediate colposcopy |
| Positive | LSIL | Immediate colposcopy |
| Any | ASC-H | Immediate colposcopy |
| Positive | ASC-US | Immediate colposcopy |
| Any | HSIL | Immediate colposcopy |
| Any | SCC | Immediate colposcopy |
| Any | AGC | Immediate colposcopy |

Table 1 Acronyms: Atypical squamous cells of undetermined significance (ASC-US); Low grade squamous intraepithelial lesion (LSIL); Atypical squamous cells-cannot exclude HSIL (ASC-H); High grade squamous intraepithelial lesion (HSIL); Squamous cell carcinoma (SCC); Abnormal glandular cells (AGC). Taken from Schiffman, M., Solomon, D., Clinical practice. Cervical-cancer screening with human papillomavirus and cytologic cotesting. N Engl J Med. 2013, 369(24): 2324-31

Pathology results obtained from biopsies taken at colposcopy are described as: Cervical intraepithelial neoplasia 1 (CIN1); Cervical Intraepithelial neoplasia 2 (CIN2); Cervical intraepithelial neoplasia 3 (CIN3); Carcinoma in situ (CIS); Invasive Cervical Carcinoma (ICC). HPV negative CIN1 is clinically equivalent to LSIL and is currently a rescreen in 6-12 months (watch and wait).

This recommended management protocol represents the current best clinical practice for testing women aged >25. It can be seen that immediate colposcopy is recommended for any women with LSIL cytology or greater (HSIL, etc.) in the absence of an HPV test. Women with LSIL who are shown to be HPV negative, are rescreened in 6-12 months.

A preferred window of opportunity for use of compositions according to the first aspect of the invention is between the time of initial diagnosis with HPV positive disease (ASC-US, LSIL, ASC-H, HSIL) until colposcopy, which usually takes approximately 2 weeks or longer, depending on waiting times. Based on what is observed at colposcopy, the decision is then made to either treat with surgery at this visit (See and Treat) or take biopsies for pathology which necessitates a further colposcopy visit approximately one month later. Clearly, if the colposcopy visits are timed appropriately, it may advantageously be that treatment according to the invention removes the need for surgery.

Compositions according to the invention are not only useful for treating actual cancers but are also surprisingly useful for preventing the development of cancer, particularly in patients that may exhibit any of the previously described pre-cancerous lesions in HPV-positive patients. Accordingly, the compositions comprising lopinavir and ritonavir may be advantageously used as a prophylactic.

The compositions may be given to subjects with a genetic disposition to developing cervical carcinomas or even those facing environmental risk (e.g. people exposed to carcinogens). In a preferred embodiment, the compositions may be given to women who are at risk of developing cervical cancer. Such women can include those who have been diagnosed as having a high-risk HPV infection (e.g. HPV16 or HPV 18) of the urino-genital tract (and particularly the cervix). At the time of diagnosis, there may not be any clinical evidence that such women have a cervical carcinoma or even precancerous cells of the cervix, yet women with such infections are believed to be at risk of developing cervical cancer. The compositions may be topically applied to the cervix of women with a viral infection of the cervix with a view to treating the viral infection and thereby preventing the development of cancer at a future date.

The compositions may be used to prevent or treat cancer as a monotherapy (i.e. use of the two inhibitors alone) or in combination with other compounds or treatments used in cancer therapy (e.g. chemotherapeutic agents, radiotherapy).

It is most preferred that the compositions are used to treat humans (i.e. women with or at risk of developing cervical cancer). However, it will be appreciated that the compositions may also have some veterinary use.

Pharmaceutical Compositions

Compositions according to the invention are formulated as a medicament that is suitable for topical application and in particular as a medicament formulated for intravaginal delivery and topical application to the cervix.

Suitable formulations include, but are not limited to, a gel, cream, paste, ointment, lotion, ovule, soft capsule, suppository, pessary, or any combination thereof. In some aspects, the pharmaceutical composition can be formulated as a gel. In some aspects, the pharmaceutical composition can be formulated as a cream. In some aspects, the pharmaceutical composition can be formulated as a paste. In some aspects, the pharmaceutical composition can be formulated as an ointment. In some aspects, the pharmaceutical composition can be formulated as a lotion. In some aspects, the pharmaceutical composition can be formulated as an ovule. In some aspects, the pharmaceutical composition can be formulated as a soft capsule. In some aspects, the pharmaceutical composition can be formulated as a suppository. In some aspects, the pharmaceutical composition can be formulated as a pessary. In some aspects, the pharmaceutical composition can be formulated as any combination of the above formulations.

In preferred embodiments, the composition is formulated such that it is suitable for topical delivery of the APIs to the cervix (e.g. as an ointment, gel, paste, cream, soft capsule, or pessary) for preventing the development of, or treating, cervical cancer (e.g. caused by high-risk types of HPV such as HPV16 or HPV18).

When used to treat (or prevent the development of) cervical cancer, the compositions can be formulated as gels, pastes, creams or ointments that may be applied directly to the cervix by techniques known to the art. Alternatively, the compositions may be formulated as a vaginal suppository (or incorporated within a pessary) according to techniques known to the art.

In other aspects, the medicaments may be in the form of an ovule. The ovule can comprise a cream or gel located within a coating, the coating configured to melt and release the cream or gel upon being administered intravaginally. Alternatively, the ovule can consist of a cream or gel that is configured to melt upon being administered intravaginally.

In one embodiment, the pharmaceutically acceptable vehicle can be a liquid and the composition can be a solution. In another embodiment, the vehicle can be a gel and the composition can be a suppository or pessary. In a further embodiment, the vehicle can be an emulsion (or other pharmaceutically acceptable base) and the composition can be a cream or paste. In a further embodiment, the vehicle can be smooth and oily and the composition can be an ointment.

Preferred compositions for use according to the invention are formulated for use as vaginal ointments comprising lopinavir and ritonavir in the weight ratios defined for compositions according to the first aspect of the invention.

Liquid vehicles may be used in preparing solutions, suspensions, emulsions, syrups, elixirs and pressurized compositions. The active ingredient can be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilizers, emulsifiers, buffers, preservatives, suspending agents, thickening agents, colours, viscosity regulators, stabilizers or osmo-regulators. Suitable examples of liquid vehicles include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). The vehicle can also be an oily ester such as ethyl oleate and isopropyl myristate. The liquid vehicle for pressurized compositions can be halogenated hydrocarbon or other pharmaceutically acceptable propellent.

The pharmaceutical composition may be a vaginal suppository. Conventional vehicles, coatings and other constituents of vaginal suppositories may be chosen by one skilled in the art to form a suppository that is characterised by the fact it comprises therapeutically effective amounts of lopinavir and ritonavir. In one embodiment vaginal suppositories typically may use polyethylene glycol as a main vehicle for lopinavir and ritonavir. The balance of the vehicle may be made up of, for example, Oleic acid, PEG 35, castor oil, purified water, gelatin, sorbitol special polyol, or any combination thereof. Lopinavir and ritonavir are virtually insoluble in water and it is preferred that such organic bases (or equivalents thereof) are formulated in such vaginal suppositories.

Preferred pharmaceutical compositions are ointments and comprise vehicles most suited for preparing ointments. Some of these formats have water present within the composition. However topical compositions which contain water are not always ideal for use with an active pharmaceutical ingredient (API) which is prone to degradation by hydrolysis because this may result in a short shelf life of the pharmaceutical product and/or the requirement to store the composition in certain conditions in order to minimize degradation of the active API. Lopinavir and ritonavir are examples of APIs which can be prone to degradation. Therefore, preferred compositions are anhydrous compositions comprising non-aqueous vehicles. Such vehicles are typically smooth oily compositions and typically contain a significant proportion (w/w) of pharmaceutically acceptable oils or fats (e.g. oleic acid). Such vehicles can contain other suitable pharmaceutical additives such as solubilizers, emulsifiers, buffers, preservatives, suspending agents, thickening agents, colours, viscosity regulators, stabilizers or osmo-regulators.

It will be appreciated that the amount of lopinavir and ritonavir in compositions according to the invention will depend up the exact components and in particular the vehicle for the composition.

By way of example only, suitable amounts of lopinavir in an ointment (e.g. the anhydrous compositions and other preferred compositions describe below) may be from about 0.1-30% w/w. In some embodiments, the amount of lopinavir in the composition can be from about 1.0-25% w/w. In some embodiments, the amount of lopinavir in the composition can be from 2.0-20% w/w. For instance, and ointment may comprise about 5%, 6%, 10% or 12% (w/w) lopinavir.

Suitable amounts of ritonavir in such compositions may be from about 0.01-3% w/w. In some embodiments, the amount of ritonavir in the composition can be from about 0.1-2.5% w/w. In some embodiments, the amount of ritonavir in the composition can be from 0.15-1.5% w/w. For instance, an ointment may comprise about 0.4775%, 0.5%, 0.625%, 0.955%, 1% or 1.25% (w/w) ritonavir.

A preferred composition may comprise about 8 to about 14% by weight of lopinavir and about 0.75 to about 1.4% by weight of ritonavir. For example, the composition may comprise by weight 10% lopinavir and 0.955% ritonavir or the composition may comprise by weight 12% lopinavir and 1% ritonavir.

Another preferred composition may comprise about 4 to about 7% by weight of lopinavir and about 0.375 to about 0.75% by weight of ritonavir. For example, the composition may comprise by weight 5% lopinavir and 0.4775% ritonavir or the composition may comprise by weight 6% weight lopinavir and 0.5% ritonavir.

Preferred Anhydrous Compositions

Preferred compositions for use according to the invention are anhydrous compositions for topical application comprising:
  a. lopinavir and ritonavir in a weight ratio of between 9:1 and 18:1; and
  b. a hydrophilic muco-adhesive agent;
wherein upon topical administration of the anhydrous composition to a site of application the anhydrous composition transforms into a muco-adhesive composition.

Advantageously, upon topical administration of the anhydrous composition to a site of application (such as the mucosal membrane of the cervix) the anhydrous composition transforms to a muco-adhesive composition. This in-situ transformation of the anhydrous composition to a muco-adhesive composition results in the muco-adhesive composition having different rheological behaviour, such as an increase in viscosity, and/or an increase in adhesiveness and/or increase in tackiness compared to the anhydrous composition.

Preferably the weight ratio of Lopinavir: ritonavir is between 10:5:1 and 13.5:1 and most preferably about 12.0:1 (w/w).

The hydrophilic muco-adhesive agent may be a non-ionic polymer or an ionic polymer. In one embodiment, the non-ionic polymer is a cellulose ether. In one embodiment, the cellulose ether is selected from methyl cellulose, ethylcellulose and hydroxypropylmethylcellulose.

In a preferred embodiment, the hydrophilic muco-adhesive agent is hydroxypropylmethylcellulose. In one embodiment, the hydroxypropylmethylcellulose has a degree of methoxy substitution of between 19 and 24% by weight and a degree of hydroxypropyl substitution of between 4 and 12% by weight.

In another embodiment, the ionic polymer is sodium polyacrylate.

Optionally, additional excipients may be included in the anhydrous composition.

In one embodiment, the anhydrous composition further comprises a thickener. A thickener is an excipient which when added to a mixture increases the viscosity of the mixture and confers the anhydrous composition with greater physical stability and/or control during delivery of the active pharmaceutical ingredient to the site of application. In one embodiment, the thickener is selected from mono di glyceride, ceresin wax, and hydrogenated vegetable oil, or a combination thereof.

In one embodiment, the anhydrous composition further comprises a stiffening agent. The stiffening agent is an excipient used to stiffen the composition so that the composition is a semi-solid at room temperature. Conveniently, the stiffening agent is a saturated free fatty acid, such as a $C_{10}$-$C_{38}$ saturated free fatty acid, such as a $C_{16}$-$C_{22}$ saturated free fatty acid. A saturated free fatty acid is a free fatty acid (i.e., the fatty acid is not bound to another molecule, such as glycerol) wherein there are no double bonds between the carbon atoms in the fatty acid. In one embodiment, the stiffening agent is selected from capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid and octatriacontanoic acid. The stiffening agent is preferably stearic acid.

In one embodiment, of the total saturated fatty acid (bound and free form fatty acid) present within the composition, at least 90% by weight, such as at least 95% by weight such as at least 98% by weight, such as at least 99% by weight, or such as at least 99.5% by weight, is in the free form, i.e., not esterified or bound to other components such as glycerol. The skilled person would be aware of methods used to determine the free fatty acid content versus the total fatty acid content. For example, the free fatty acid content can be measured by reacting the free fatty acid with a chromogenous compound, thus changing the frequency that the chromogenous compound absorbs electromagnetic radiation. Thus, the concentration of the chromogenous compound reacted can be determined by monitoring the chromogenous compound using a suitable wavelength which in turn can be used to determine the free fatty acid content in the sample.

In one embodiment, the saturated free fatty acid is not in the form of a triglyceride or polysorbate.

In one embodiment, the anhydrous composition further comprises a solvent for lopinavir and ritonavir.

In one embodiment, the solvent is selected from an unsaturated free fatty acid, PEG castor oil, diethylene glycol monoethyl ether, propylene glycol, polyethylene glycol, and a medium chain triglyceride. Fatty acids are usually derived from triglycerides or phospholipids. Glycerol has three hydroxyl functional groups, which can be esterified with one, two, or three fatty acids to form mono-, di-, or triglycerides respectively. Phospholipid molecules consist of two hydrophobic fatty acid "tails" and a hydrophilic "head" consisting of a phosphate group. These two components are joined together by a glycerol molecule. Both triglyceride and phospholipids comprise fatty acids in a bound state. Conversely, free fatty acids are fatty acids which are not bound, that is they are not esterified. An unsaturated free fatty acid is a free fatty acid wherein there is at least one double bond between carbon atoms in the fatty acid. In one embodiment, the solvent is an unsaturated free fatty acid.

In one embodiment, the unsaturated free fatty acid is selected from oleic acid, linoleic acid, alpha-linoleic acid, palmitoleic acid, gondoic acid, and ricinoleic acid.

In one embodiment, the unsaturated free fatty acid is oleic acid.

In one embodiment, of the total unsaturated fatty acid (bound and free form unsaturated fatty acid) present within the composition, at least 90% by weight, such as at least 95% by weight such as at least 98% by weight, such as at least 99% by weight, or such as at least 99.5% by weight, is in the free form, i.e., not esterified or bound to other components such as glycerol. The skilled person would be aware of methods used to determine the free fatty acid content versus the total fatty acid content. For example, the free fatty acid content can be measured by reacting the free fatty acid with a chromogenous compound, thus changing the frequency that the chromogenous compound absorbs electromagnetic radiation. Thus, the concentration of the chromogenous compound reacted can be determined by monitoring the chromogenous compound using a suitable wavelength which in turn can be used to determine the free fatty acid content in the sample.

It is to be understood that free fatty acids products that are commercially available may contain small amounts of other free fatty acids. For example, oleic acid typically contains 7-12% saturated free fatty acids, such as stearic and palmitic acid, together with other unsaturated free fatty acids, such as linoleic acid (Handbook of Pharmaceutical Excipients, $2^{nd}$ Edition, see entry for Oleic acid). The terms saturated free fatty acid or unsaturated free fatty acid are to be understood as meaning the saturated free fatty acid or the unsaturated free fatty acid are of Pharmacopeia grade, such as the US Pharmacopeia and/or the British Pharmacopeia, and that the saturated free fatty acid or unsaturated free fatty acid may contain small amounts of other free fatty acids.

In one embodiment, the unsaturated free fatty acid is not in the form of a triglyceride or polysorbate.

The total fatty acid (unsaturated and saturated fatty acids in the bound and free form) present within the composition may be at least 90% by weight, such as at least 95% by weight such as at least 98% by weight, such as at least 99% by weight, or such as at least 99.5% by weight, in the free form, i.e., not esterified or bound to other components such as glycerol.

In one embodiment, the anhydrous composition further comprises oleic acid and stearic acid.

In one embodiment, the anhydrous composition further comprises oleic acid, stearic acid, mono di glyceride, ceresin wax, and hydrogenated vegetable oil In one embodiment, there is provided an anhydrous composition for topical application comprising:
 a. ritonavir;
 b. lopinavir;
 c. hydroxypropylmethylcellulose;
 d. oleic acid;
 e. stearic acid; and
 f. butylated hydroxytoluene In one embodiment, the anhydrous composition comprises:
 a. about 1.2 to about 1.4% by weight of ritonavir;
 b. about 9 to about 11% by weight of lopinavir;
 c. about 0.5 to about 1.5% by weight of hydroxypropylmethylcellulose;
 d. about 55 to about 65% by weight of oleic acid;
 e. about 28 to about 32% by weight of stearic acid; and
 f. about 00.5 to about 0.5% by weight of butylated hydroxytoluene;
wherein all % are by weight based upon the total weight of the composition.

In another embodiment, the anhydrous composition comprises:
 a. about 0.5 to about 0.7% by weight of ritonavir;
 b. about 4 to about 6% by weight of lopinavir;
 c. about 0.5 to about 1.5% by weight of hydroxypropylmethylcellulose;
 d. about 55 to about 65% by weight of oleic acid;
 e. about 28 to about 32% by weight of stearic acid; and
 f. about 0.05 to about 0.5% by weight of butylated hydroxytoluene;
wherein all % are by weight based upon the total weight of the composition.

A preferred anhydrous composition comprises:
a. ritonavir;
b. lopinavir;
c. hydroxypropylmethylcellulose;
d. oleic acid;
e. stearic acid;
f. butylated hydroxytoluene;
g. mono diglyceride;
h. ceresin wax;
i. hydrogenated vegetable oil;
j. polyoxyl 100 stearate; and
k. glycerol monooleate;

In one embodiment, the anhydrous composition comprises:
a. about 0.9 to about 1.1% by weight of ritonavir;
b. about 9 to about 11% by weight of lopinavir;
c. about 0.5 to about 1.5% by weight of hydroxypropylmethylcellulose;
d. about 55 to about 65% by weight of oleic acid;
e. about 4 to about 5% of stearic acid;
f. about 0.1 to about 0.3% by weight of butylated hydroxytoluene;
g. about 4 to about 6% by weight of mono diglyceride;
h. about 5 to about 7% by weight of ceresin wax;
i. about 9 to about 11% by weight of hydrogenated vegetable oil;
j. about 1 to about 3% by weight of polyoxyl 100 stearate; and
k. about 2 to about 4% by weight of glycerol monooleate;
wherein all % are by weight based upon the total weight of the composition In one embodiment, the anhydrous composition comprises:
a. about 0.9 to about 1.1% by weight of ritonavir;
b. about 11 to about 13% by weight of lopinavir;
c. about 0.5 to about 1.5% by weight of hydroxypropylmethylcellulose;
d. about 50 to about 60% by weight of oleic acid;
e. about 4 to about 5% of stearic acid;
f. about 0.1 to about 0.3% by weight of butylated hydroxytoluene;
g. about 4 to about 6% by weight of mono diglyceride;
h. about 5 to about 7% by weight of ceresin wax;
i. about 9 to about 11% by weight of hydrogenated vegetable oil;
j. about 1 to about 3% by weight of polyoxyl 100 stearate; and
k. about 2 to about 4% by weight of glycerol monooleate;
wherein all % are by weight based upon the total weight of the composition.

In one embodiment, the anhydrous composition comprises:
a. about 0.4 to about 0.6% by weight of ritonavir;
b. about 4 to about 6% by weight of lopinavir;
c. about 0.5 to about 1.5% by weight of hydroxypropylmethylcellulose;
d. about 55 to about 65% by weight of oleic acid;
e. about 4 to about 5% of stearic acid;
f. about 0.1 to about 0.3% by weight of butylated hydroxytoluene;
g. about 4 to about 6% by weight of mono diglyceride;
h. about 5 to about 7% by weight of ceresin wax;
i. about 9 to about 11% by weight of hydrogenated vegetable oil;
j. about 1 to about 3% by weight of polyoxyl 100 stearate; and
k. about 2 to about 4% by weight of glycerol monooleate;
wherein all % are by weight based upon the total weight of the composition.

In one embodiment, the anhydrous composition comprises:
a. about 0.4 to about 0.6% by weight of ritonavir;
b. about 5 to about 7% by weight of lopinavir;
c. about 0.5 to about 1.5% by weight of hydroxypropylmethylcellulose;
d. about 55 to about 65% by weight of oleic acid;
e. about 4 to about 5% of stearic acid;
f. about 0.1 to about 0.3% by weight of butylated hydroxytoluene;
g. about 4 to about 6% by weight of mono diglyceride;
h. about 5 to about 7% by weight of ceresin wax;
i. about 9 to about 11% by weight of hydrogenated vegetable oil;
j. about 1 to about 3% by weight of polyoxyl 100 stearate; and
k. about 2 to about 4% by weight of glycerol monooleate;
wherein all % are by weight based upon the total weight of the composition.

Other Preferred Compositions

Another preferred composition for use according to the invention is a pharmaceutical composition comprising:
a. an unsaturated free fatty acid;
b. a stiffening agent; and
c. lopinavir and ritonavir in a weight ratio of between 10:1 and 18:1;
wherein the unsaturated free fatty acid is present at a level of at least 20% by weight of the total pharmaceutical composition weight and wherein the pharmaceutical composition is a semi-solid at room temperature.

Preferably the weight ratio of Lopinavir: ritonavir is between 10:5:1 and 13.5:1 and most preferably about 12.0:1 (w/w).

Conventional compositions employ vegetable oils and/or polysorbates as agents to thicken the composition. It has been advantageously established that an unsaturated free fatty acid and a stiffening agent can be used to prepare a pharmaceutical composition which is a semi-solid at room temperature that can be present in a stationary material state until an external stress is applied resulting in flow of the material. Such an external stress can be the application of the composition to a target tissue (i.e. the cervix) and the inventors have found that such compositions are particularly effective for delivering lopinavir and ritonavir to the target tissue.

Advantageously, the pharmaceutical composition only comprises fats in the form of free fatty acids (unsaturated free fatty acid and/or saturated free fatty acid), for example all fatty acids present in the composition are in the form of a free fatty acid. This allows the pharmaceutical composition to be manufactured at room temperature which is advantageous when the at least one active pharmaceutical is prone to degradation, and wherein the rate and/or extent of degradation is increased when the active pharmaceutical ingredient is exposed to heat.

The unsaturated free fatty acid may be as described above for anhydrous compositions and is preferably oleic acid.

The stiffening agent may be as described above for anhydrous compositions and is preferably stearic acid.

Such pharmaceutical compositions may optionally include a muco-adhesive agent and other excipients as described above for anhydrous compositions.

Preferred pharmaceutical compositions are disclosed in Example 7 and Tables 2-5 and manufactured as disclosed in Example 7 or Example 10.1.

Dosing

It will be appreciated that the amount of lopinavir and ritonavir required is determined by biological activity and bioavailability, which in turn depends, in part, on the precise mode of administration, the physicochemical properties of the composition employed, and whether the compositions are being used as a monotherapy or in a combined therapy with other oral or topical medicines. Indeed, it is also possible that the at least one active pharmaceutical ingredient could be topically applied in addition to oral dosing of the same compounds or other active pharmaceutical ingredient(s). The frequency of administration will also be influenced by the abovementioned factors and particularly the half-life of the active pharmaceutical ingredients within the subject being treated.

Daily doses may be given as a single administration (e.g. as an ointment, soft capsule, vaginal suppository, ovule or pessary). Preferably the compositions are administered once a day and preferably in the evening before going to sleep. Alternatively, administration may be twice or more times during a day. As an example, the compositions may be topically administered at least once a day, such as once a day or twice a day.

Optimal dosages to be administered may be determined by those skilled in the art, and will vary with the strength of the preparation, the mode of administration, and the advancement of the disease condition. Additional factors depending on the particular subject being treated will result in a need to adjust dosages, including, for example, subject age, weight, diet, and time of administration.

Suitable amounts of lopinavir to be given are a daily dose of between about 0.1 mg to about 10.0 g. In some embodiments, the daily dose of lopinavir can be from about 10 mg to about 5.0 g. In some embodiments, the daily dose of lopinavir can be from about 25 mg to about 1.0 g. Conveniently, the daily dose of lopinavir may be between 25 mg and 500 mg (e.g. about 300 mg or 150 mg).

Suitable amounts of ritonavir to be given are a daily dose of about 0.01 mg to about 1.0 g. In some embodiments, the daily dose of ritonavir can be from about 1.0 mg to about 250.0 mg. In some embodiments, the daily dose of ritonavir can be from about 2.5 mg to about 100 mg. Conveniently, the daily dose of ritonavir may be between 5 mg and 50 mg (e.g. about 25 mg, 28.65 mg, 12.5 mg or 14.325 mg).

In one embodiment, about 300 mg of lopinavir and about 28.65 mg of ritonavir per day may be administered to the cervix of a woman.

In another embodiment, about 150 mg of lopinavir and about 14.325 mg of ritonavir per day may be administered to treat the cervix of a woman.

In another embodiment, about 300 mg of lopinavir and about 25 mg of ritonavir per day may be administered to treat the cervix of a woman.

In another embodiment, about 150 mg of lopinavir and about 12.5 mg of ritonavir per day may be administered to treat the cervix of a woman.

It will be appreciated that the amount of a composition which needs to be administered to a subject will depend upon the concentration of lopinavir and ritonavir in the composition and also the size of the lesion which needs to be treated. By way of example preferred ointments (e.g. preferred anhydrous composition discussed above) may be administered by a syringe in volumes sufficient to administer 0.5-15.0 g, preferably in volumes sufficient to administer 1.0-7.5 g of the composition.

In one embodiment about 3.0 g of a composition may be administered to a subject per day. Such dosage forms may comprise about 300 mg of lopinavir and about 28.65 mg of ritonavir; or about 150 mg of lopinavir and about 14.325 mg of ritonavir.

In another embodiment, about 2.5 g of a composition may be administered to a subject per day. Such dosage forms may comprise about 300 mg of lopinavir and about 25 mg of ritonavir; or about 150 mg of lopinavir and about 12.5 mg of ritonavir.

In one preferred embodiment about 3.0 g of the ointment disclosed in Table 2 or Table 3 is administered to the cervix, by a syringe applicator, as a once per day application (preferably in the evening before retiring for the night).

In a most preferred embodiment about 2.5 g of the ointment disclosed in Table 4 or Table 5 is administered to the cervix, by a syringe applicator, as a once per day application (preferably in the evening before retiring for the night).

Prefered Treatment Regimens

The medicament may be administered to a subject for as long as treatment is required. The length of time for which treatment will be required will depend upon the exact condition being treated or prevented and its severity. A skilled person will appreciate that treatment should be maintained in view of a number of factors which will include any requirement to eradicate any oncogenic virus (e.g. HPV); to reduce or eradicate cells with a precancerous or cancerous phenotype; or to shrink or eradicate any tumour or other lesion (e.g. a wart).

In one embodiment a course of treatment may be for 2-4 weeks, 7-21 days or for about 14 days. After this time a clinician may assess whether the course of treatment has been successful. A decision may then be made whether or not to continue treatment.

It will be appreciated that a clinician may wish to take into account menstruation when deciding on a treatment regimen for women with conditions relating to the cervix. Accordingly, a preferred treatment regimen may be for about 14-21 days and can be administered between menses. A clinician may elect to stop topical treatment of the cervix during menses and recommence a new course of treatment in the next menstrual cycle. By way of example, a preferred treatment regimen can be: (1) 14-21 days of administration; (2) followed by 1-14 days without treatment (during which menses may occur if treating the cervix); and (3) a further cycle of 14-21 days of treatment if this is considered medically necessary.

In a preferred embodiment, the cervix of a woman may be treated such that she receives about 300 mg of lopinavir and about 28.65 mg ritonavir per day for 14-21 days; treatment can then be stopped for 1-14 days and a clinical reassessment can be conducted; then, if necessary a second treatment cycle of about 300 mg of lopinavir and about 28.65 mg ritonavir per day can be administered for a further 14-21 days. After the second cycle a further clinical assessment can be made and a decision made about whether or not subsequent treatment cycles are required.

In another preferred embodiment, the cervix of a woman may be treated such that she receives about 150 mg of lopinavir and about 14.325 mg ritonavir per day for 14-21 days; treatment can then be stopped for 1-14 days and a clinical reassessment can be conducted; then, if necessary a second treatment cycle of about 150 mg of lopinavir and about 14.325 mg ritonavir per day can be administered for a further 14-21 days. After the second cycle a further clinical assessment can be made and a decision made about whether or not subsequent treatment cycles are required.

In another preferred embodiment, the cervix of a woman may be treated such that she receives about 300 mg of lopinavir and about 25 mg ritonavir per day for 14-21 days; treatment can then be stopped for 1-14 days and a clinical reassessment can be conducted; then, if necessary a second treatment cycle of about 300 mg of lopinavir and about 25 mg ritonavir per day can be administered for a further 14-21 days. After the second cycle a further clinical assessment can be made and a decision made about whether or not subsequent treatment cycles are required.

In another preferred embodiment, the cervix of a woman may be treated such that she receives about 150 mg of lopinavir and about 12.5 mg ritonavir per day for 14-21 days; treatment can then be stopped for 1-14 days and a clinical reassessment can be conducted; then, if necessary a second treatment cycle of about 150 mg of lopinavir and about 12.5 mg ritonavir per day can be administered for a further 14-21 days. After the second cycle a further clinical assessment can be made and a decision made about whether or not subsequent treatment cycles are required Each of these regimens may most preferably involve administering (once a day) to a subject of 0.5-15.0 g of an ointment according to the invention, preferably 1.0-7.5g of an ointment and most preferably about 2.5 g or about 3.0 g of the ointment.

A preferred treatment regimen is described in Example 8.

Treatment of HPV Related Dysplasia

In preferred embodiments of the invention the pharmaceutical compositions may be used to treat female subjects having an HPV related dysplasia of the cervix.

As used herein, "dysplasia" encompasses pre-invasive lesions and cancer. HPV related pre-invasive lesions include high grade squamous intraepithelial lesion (HSIL), atypical squamous cells of undetermined significance (ASCUS), and low grade squamous intraepithelial lesion (LSIL). HPV related cancers include, for example, cervical intraepithelial neoplasia (CIN) and invasive cervical cancer (ICC).

The disclosed methods and treatment regimens can be used to treat HPV related dysplasia. In some aspects, for example, the disclosed methods and treatment regimens can be used to treat HSIL. In some aspects, the disclosed methods and treatment regimens can be used to treat ASCUS. In other aspects, the disclosed methods and treatment regimens can be used to treat LSIL. In other aspects, the disclosed methods and treatment regimens can be used to treat CIN. In yet other embodiments, the disclosed methods and treatment regimens can be used to treat ICC. Additionally, the disclosed methods and treatment regimens can be used to inhibit the progression of HPV related dysplasia. In some aspects, for example, the disclosed methods and treatment regimens can be used to inhibit the progression of HSIL. In some aspects, the disclosed methods and treatment regimens can be used to inhibit the progression of ASCUS. In other aspects, the disclosed methods and treatment regimens can be used to inhibit the progression of LSIL. In other aspects, the disclosed methods and treatment regimens can be used to inhibit the progression of CIN. In yet other embodiments, the disclosed methods and treatment regimens can be used to inhibit the progression of ICC.

The pharmaceutical composition can reduce the severity of the HPV related dysplasia. Severity of the HPV related dysplasia can be measured and graded by, for example, changes in histology. Methods of performing histology on biopsies of HPV-related lesions are well known in the art. In some embodiments, for example, the disclosed compositions can reduce the severity of CIN 3. In some aspects, the disclosed compositions can reduce the severity of CIN3 to CIN2. In other aspects, the disclosed compositions can reduce the severity of CIN3 to CIN1. In other aspects, the disclosed compositions can reduce the severity of CIN3 to HPV negative. In other aspects, the disclosed compositions can reduce the severity of CIN2 to CIN1. In other aspects, the disclosed compositions can reduce the severity of CIN2 to HPV negative. In other aspects, the disclosed compositions can reduce the severity of CIN1 to HPV negative.

A subject may have a cervical cytology (e.g., from a PAP smear) of HSIL, ASCUS, or LSIL. Administration of the pharmaceutical composition to such a subject can reduce the cervical cytology. In some aspects, the cervical cytology is reduced from HSIL to a normal cytology. In some aspects, the cervical cytology is reduced from HSIL to ACSUS. In some aspects, the cervical cytology is reduced from HSIL to LSIL. In some aspects, the cervical cytology is reduced from ACSUS to a normal cytology. In some aspects, the cervical cytology s reduced from LSIL to a normal cytology.

Histological assessments to evaluate and/or grade the severity of the HPV related dysplasia and cytological screening can be performed at any suitable time period prior to, during, and/or post-treatment with the disclosed compositions. In some embodiments, the methods further comprise post-treatment monitoring of the subject. Suitable timeframes for post-treatment monitoring include, but are not limited to, 4 weeks, 8 weeks, 12 weeks, 16 weeks, 20 weeks, 24 weeks, 28 weeks, 32 weeks, 36 weeks, 40 weeks, 44 weeks, 48 weeks, or 52 weeks following treatment with the disclosed pharmaceutical compositions. In some aspects, for example, a histological assessment can be performed at baseline (prior to treatment) and 6 months post-treatment to assess changes in CIN status. In other aspects, a cytological screen can be performed at baseline and 6 months post-treatment to assess changes in cervical cytology. In yet other aspects, a histological assessment and cytological screen can be performed at baseline and 6 months post-treatment to assess changes in CIN status and cervical cytology, respectively.

The extent and grade of an HPV related dysplasia can be reduced during a period of from about 4 weeks to about 52 weeks following administering said composition. In some aspects, the extent and histological grade of the dysplasia can be reduced from about 4 weeks to about 46 weeks following administering said composition. In some aspects, the extent and histological grade of the dysplasia can be reduced from about 4 weeks to about 40 weeks following administering said composition. In some aspects, the extent and histological grade of the dysplasia can be reduced from about 4 weeks to about 34 weeks following administering said composition. In some aspects, the extent and histological grade of the dysplasia can be reduced from about 4 weeks to about 28 weeks following administering said composition. In some aspects, the extent and histological grade of the dysplasia can be reduced from about 4 weeks to about 24 weeks following administering said composition. In some aspects, the extent and histological grade of the dysplasia can be reduced from about 4 weeks to about 18 weeks following administering said composition. In some aspects, the extent and histological grade of the dysplasia can be reduced from about 4 weeks to about 12 weeks following administering said composition. In some aspects, the extent and histological grade of the dysplasia can be reduced from about 6 weeks to about 10 weeks following administering said composition. In some aspects, the extent and histological grade of the dysplasia can be reduced from about 8 weeks to about 52 weeks following administering said composition. In some aspects, the extent and histological grade of the dysplasia can be reduced from about 12 weeks to about 52 weeks following administering said composition. In some aspects, the extent and histological grade of the dysplasia can be reduced from about 18 weeks to about 52 weeks following administering said composition. In some aspects, the extent and histological grade of the dysplasia can be reduced from about 24 weeks to about 52 weeks following administering said composition. In some aspects, the extent and histological grade of the dysplasia can be reduced from about 30 weeks to about 52 weeks following administering said composition. In some aspects, the extent and histological grade of the dysplasia can be reduced from about 36 weeks to about 52 weeks following administering said composition. In some aspects, the extent and histological grade of the dysplasia can be reduced about 42 weeks to about 52 weeks following administering said composition. In some aspects, the extent and histological grade of the dysplasia can be reduced from about 48 weeks to about 52 weeks following administering said composition.

In some aspects, the extent and histological grade of the dysplasia can be reduced within about 4 weeks following administering compositions according to the invention. In some aspects, the extent and histological grade of the dysplasia can be reduced within about 5 weeks following administering said composition. In some aspects, the extent and histological grade of the dysplasia can be reduced within about 6 weeks following administering said composition. In some aspects, the extent and histological grade of the dysplasia can be reduced within about 7 weeks following administering said composition. In some aspects, the extent and histological grade of the dysplasia can be reduced within about 8 weeks following administering said composition. In some aspects, the extent and histological grade of the dysplasia can be reduced within about 9 weeks following administering said composition. In some aspects, the extent and histological grade of the dysplasia can be reduced within about 10 weeks following administering said composition. In some aspects, the extent and histological grade of the dysplasia can be reduced the extent and histological grade of the dysplasia can be reduced within about 11 weeks following administering said composition. In some aspects, the extent and histological grade of the dysplasia can be reduced within about 12 weeks following administering said composition. In some aspects, the extent and histological grade of the dysplasia can be reduced within about 16 weeks following administering said composition. In some aspects, the extent and histological grade of the dysplasia can be reduced within about 20 weeks following administering said composition. In some aspects, the extent and histological grade of the dysplasia can be reduced within about 24 weeks following administering said composition. In some aspects, the extent and histological grade of the dysplasia can be reduced within about 28 weeks following administering said composition. In some aspects, the extent and histological grade of the dysplasia can be reduced within about 32 weeks following administering said composition. In some aspects, the extent and histological grade of the dysplasia can be reduced within about 36 weeks following administering said composition. In some aspects, the extent and histological grade of the dysplasia can be reduced within about 40 weeks following administering said composition. In some aspects, the extent and histological grade of the dysplasia can be reduced within about 44 weeks following administering said composition. In some aspects, the extent and histological grade of the dysplasia can be reduced within about 48 weeks following administering said composition. In some aspects, the extent and histological grade of the dysplasia can be reduced within about 52 weeks following administering said composition.

The cervical cytology grade can similarly be reduced from about 4 weeks to about 52 weeks following administering said composition. In some aspects, the cervical cytology grade be reduced from about 4 weeks to about 46 weeks following administering said composition. In some aspects, the cervical cytology grade be reduced from about 4 weeks to about 40 weeks following administering said composition. In some aspects, the cervical cytology grade be reduced from about 4 weeks to about 34 weeks following administering said composition. In some aspects, the cervical cytology grade be reduced from about 4 weeks to about 28 weeks following administering said composition. In some aspects, the cervical cytology grade be reduced from about 4 weeks to about 24 weeks following administering said composition. In some aspects, the cervical cytology grade be reduced from about 4 weeks to about 18 weeks following administering said composition. In some aspects, the cervical cytology grade be reduced from about 4 weeks to about 12 weeks following administering said composition. In some aspects, the cervical cytology grade be reduced from about 6 weeks to about 10 weeks following administering said composition. In some aspects, the cervical cytology grade be reduced from about 8 weeks to about 52 weeks following administering said composition. In some aspects, the cervical cytology grade be reduced from about 12 weeks to about 52 weeks following administering said composition. In some aspects, the cervical cytology grade be reduced from about 18 weeks to about 52 weeks following administering said composition. In some aspects, the cervical cytology grade be reduced from about 24 weeks to about 52 weeks following administering said composition. In some aspects, the cervical cytology grade be reduced from about 30 weeks to about 52 weeks following administering said composition. In some aspects, the cervical cytology grade be reduced from about 36 weeks to about 52 weeks following administering said composition. In some aspects, the cervical cytology grade be reduced from about 42 weeks to about 52 weeks following administering said composition. In some aspects, the cervical cytology grade be reduced from about 48 weeks to about 52 weeks following administering said composition.

In some aspects, the cervical cytology grade reduced within about 4 weeks following administering said composition. In some aspects, the cervical cytology grade reduced within about 5 weeks following administering said composition. In some aspects, the cervical cytology grade reduced within about 6 weeks following administering said composition. In some aspects, the cervical cytology grade reduced within about 7 weeks following administering said composition. In some aspects, the cervical cytology grade reduced within about 8 weeks following administering said composition. In some aspects, the cervical cytology grade reduced within about 9 weeks following administering said composition. In some aspects, the cervical cytology grade reduced within about 10 weeks following administering said composition. In some aspects, the cervical cytology grade reduced within about 11 weeks following administering said composition. In some aspects, the cervical cytology grade reduced within about 12 weeks following administering said composition. In some aspects, the cervical cytology grade reduced within about 16 weeks following administering said composition. In some aspects, the cervical cytology grade reduced within about 20 weeks following administering said composition. In some aspects, the cervical cytology grade reduced within about 24 weeks following administering said composition. In some aspects, the cervical cytology grade reduced within about 28 weeks following administering said composition. In some aspects, the cervical cytology grade reduced within about 32 weeks following administering said composition. In some aspects, the cervical cytology grade reduced within about 36 weeks following administering said composition. In some aspects, the cervical cytology grade reduced within about 40 weeks following administering said composition. In some aspects, the cervical cytology grade reduced within about 44 weeks following administering said composition. In some aspects, the cervical cytology grade reduced within about 48 weeks following administering said composition. In some aspects, the cervical cytology grade reduced within about 52 weeks following administering said composition.

The therapeutically effective dose of the disclosed pharmaceutical compositions can be administered for about 1 week to about 4 weeks. After this time a clinician may assess whether the course of treatment has been successful. A decision may then be made whether or not to continue treatment.

In some embodiments, the composition induces apoptosis of HPV infected cells.

EXAMPLES

Example 1

Assessment of the effects of 8:1-16:1 w/w ratios of Lopinavir:Ritonavir at a total API concentration of 20 μM on E6/E7 Immortalised non-transformed endocervical cells E6/E7 endocervical cells are a non-transformed cell line with a phenotype similar to the phenotype found in HPV related cervical dysplasia. The cell line therefore represents a good model for evaluating the effect of lopinavir and ritonavir on precancerous and early stage cancerous conditions. For instance, HPV related Dysplasias CIN1- CIN3.

1.1 METHODS 1.1.1 Cell Culture

E6/E7 cells were maintained by standard methods in RPMI growth medium containing 5% Fetal Calf Serum (FCS) at 5% $CO_2$ and 37° C.

Experiments were conducted on cells seeded from a T75 confluent starter culture to a T25 flask. The cells were cultured in the T25 flasks for 6 days. The first 3 days followed standard culture conditions whereas for days 4-6 the cells were grown in growth medium without FCS. This step synchronised cells in the growth cycle and the inventors found this step improved the performance of subsequent assay steps.

1.1.2 Treatments

After the sixth day (1.1.1), culture was continued for a further 3 days in RPMI growth medium containing 5% FCS and a total API concentration of 20 μM and with lopinavir and ritonavir present in the ratios discussed in the results section.

1.1.3 DNA Fragmentation Assays in a NC3000 Image Cytometer (Chemometec Ltd, Norway).

After the final day of culture with the APIs, the cells were trypsinised, pelleted and washed with PBS using standardized procedures. The cells were then fixed in 70% ethanol for a minimum of 4 hours, washed in PBS, counted and then stained with DAPI according to the manufacturers DNA Fragmentation assay procedure (Chemometec Ltd, Norway).

Stained cells were then analyzed using eight chamber slides with the NC3000 Image Cytometer. A representative cell cycle/DNA fragmentation profile is shown in FIG. 3(B). the cytometer distinguished cells from 4 phases of the cell cycle (M1-M4 in FIG. 3(B) which corresponds to Sub G1(dead cells), G1, S and G2) depending on detecting characteristic DNA staining in each cell in the assayed sample. Each data point on the Box and Whisker Plots is the product of four such assays which were analyzed for statistical significance with pairwise permutation test using the R program. The percentage of cells undergoing apoptotic DNA fragmentation (Sub G1) versus those which have intact 2N DNA (G1) was calculated and the data plotted as bar charts for cells treated with the specified ratios of lopinavir: ritonavir.

1.2 RESULTS

FIG. 1 represents data presented as the percentage of cells which are undergoing apoptotic DNA fragmentation (Sub G1) versus those which have intact 2N DNA (G1) following treatment with lopinavir and ritonavir at 8:1, 10:1, 12:1, 14:1 and 16:1 (w/w).

The inventors were surprised to note that a statistically significant peak of apoptotic activity (corresponding to induced cell death of the E6/E7 cells) was apparent for a 12:1 (w/w) ratio of the APIs (See FIG. 1).

This illustrates that lopinavir and ritonavir, in ratios according to the invention, have improved efficacy for treating pre-invasive pathologies, and particularly HOV-related pathologies, of the cervix (CIN1-CIN3).

Example 2

Assessment of the effects of 8:1-14:1 w/w ratios of Lopinavir:Ritonavir at a total API concentration of 20 μM on HPV18 positive HeLa cervical carcinoma cells The effect of different ratios of lopinavir and ritonavir were assessed in HeLa cells. HeLa cells are HPV18 positive cervical carcinoma cell line and are a good model HPV-related malignant disease (e.g. Invasive cervical cancer (ICC)).

2.1 METHODS

The methods described in 1.1 were followed except:

2.1.1: The cells were cultured in the T25 flasks for 2 days. The first day followed standard culture conditions whereas for the second the cells were grown in growth medium without FCS.

2.1.2: Culture was continued for a further 2 days in RPMI growth medium containing 5% FCS and a total API concentration of 20 μM and with lopinavir and ritonavir present in the ratios discussed in the results section.

2.2 RESULTS

Figure 2:
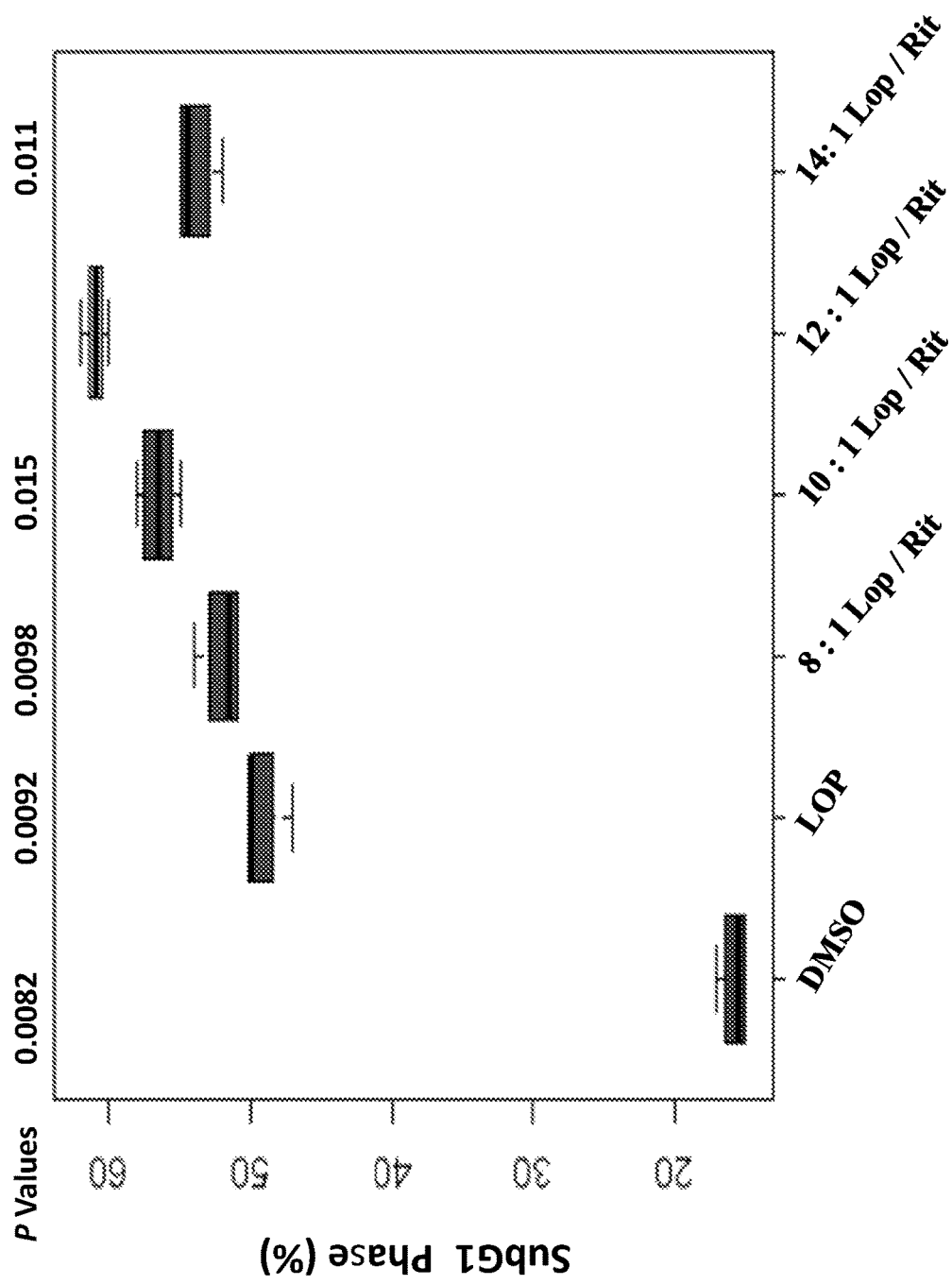
FIG. 2 represents (A) a bar chart illustrating the effects of various weight ratios of lopinavir:ritonavir on inducing apoptosis in HPV18+ve HeLA cells as discussed in Example 2; and (B) bar chart illustrating the effects of a 14:1 w/w ratios of lopinavir:ritonavir on inducing apoptosis in a further experiment conducted with HPV18+ve HeLA (also as discussed in Example 2)

FIG. 2(A) represents data presented as the percentage of cells which are undergoing apoptotic DNA fragmentation (Sub G1) versus those which have intact 2N DNA (G1)

following treatment with DMSO (control); 20 μM lopinavir alone; and lopinavir and ritonavir at 8:1, 10:1, 12:1, and 14:1 (w/w).

The inventors noted that the apoptotic activity caused by lopinavir increased when ritonavir was included at a ratio of 8:1 and 10:1 and, as was the case for E6/E7 cells, peaked for a 12:1 (w/w) ratio of the APIs.

Figure 2B:
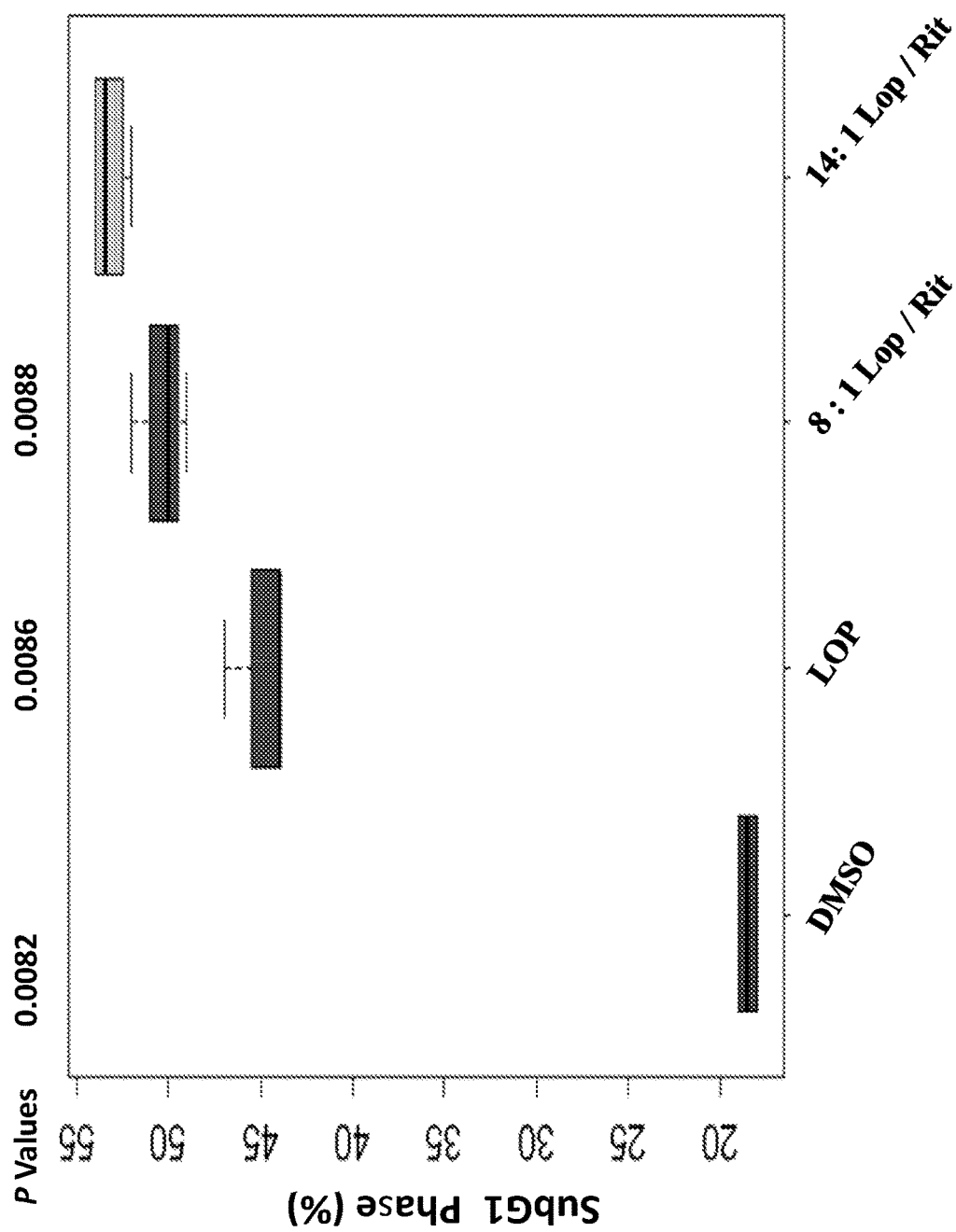

FIG. 2(B) represents data from a second experiment examining the effects of DMSO (control); 20 μM lopinavir alone; and lopinavir and ritonavir at 8:1 and 14:1 (w/w). The graph illustrates that lopinavir:ritonavir in a ratio according to the invention (14:1) was significantly more effective for killing HeLa cells than lopinavir alone or the APIs at a ratio of 8:1.

This illustrates that lopinavir and ritonavir, in ratios according to the invention, will have improved efficacy for treating HPV-related malignant disease and ICC.

Example 3

Assessment of the effects of 12:1 w/w ratios of Lopinavir:Ritonavir at a total API concentration of 20 μM on HPV16 positive SiHa cervical carcinoma cells The effect of different ratios of lopinavir and ritonavir were assessed in SiHa cells. SiHa cells are a HPV16 positive cervical carcinoma cell line and are a good model for HPV-related malignant disease and ICC Invasive cervical cancer (ICC).

3.1 METHODS

The methods described in 1.1 were followed except:

3.1.1: The cells were cultured in the T25 flasks for 7 days. The 4 days followed standard culture conditions whereas for days 5-7 the cells were grown in growth medium without FCS.

3.1.2: Culture was continued for a further 3 days in RPMI growth medium containing 5% FCS and a total API concentration of 20 μM and with lopinavir and ritonavir present in the ratios discussed in the results section.

3.2 RESULTS

Figure 3:
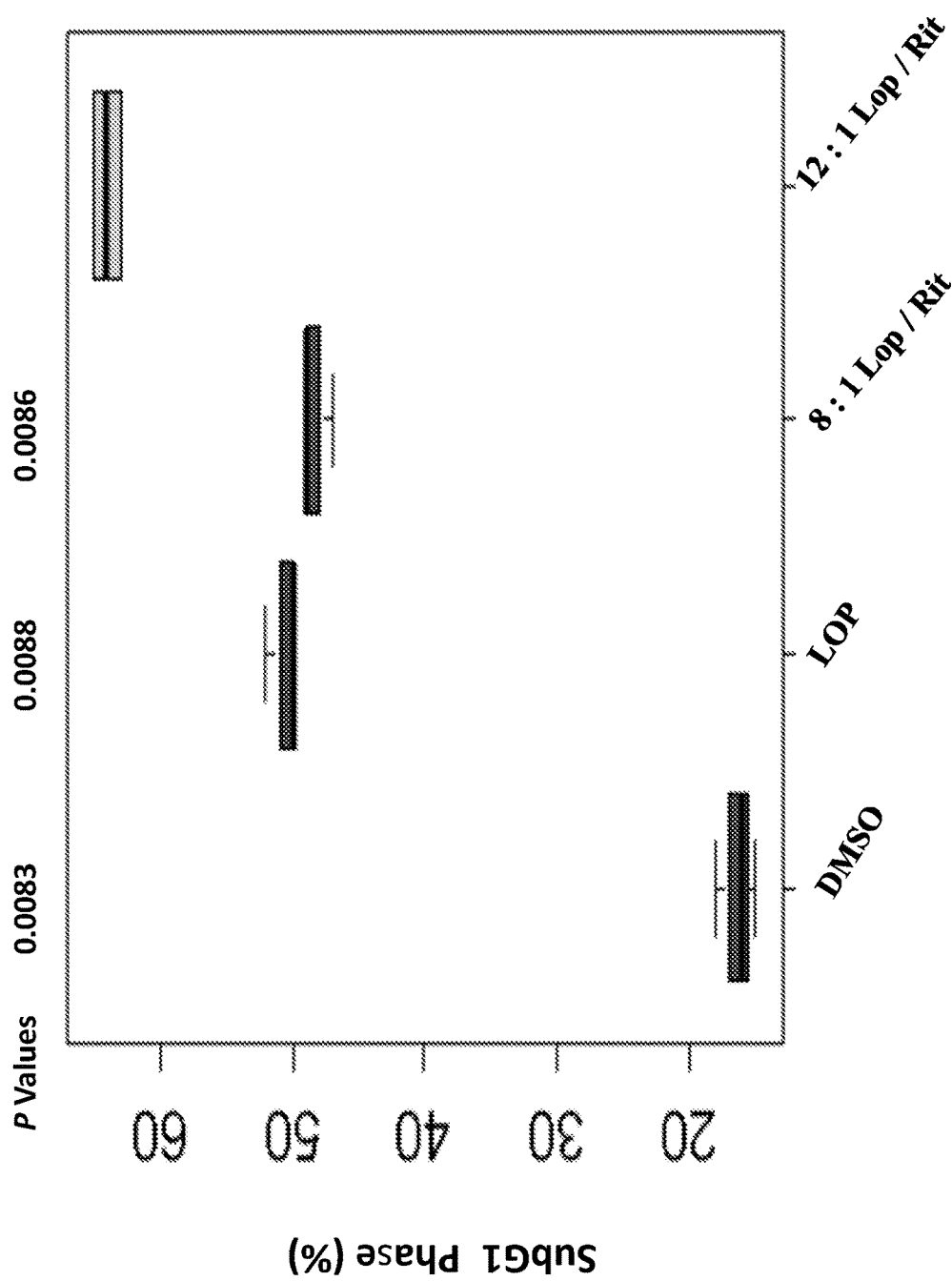
FIG. 3 represents: (A) a bar chart illustrating the effects of 12:1 weight ratios of lopinavir:ritonavir on inducing apoptosis in HPV16+ve SiHa cells as discussed in Example 3; and (B) illustrative cytometer results from which the data in the bar charts are based.
Figure 3B:
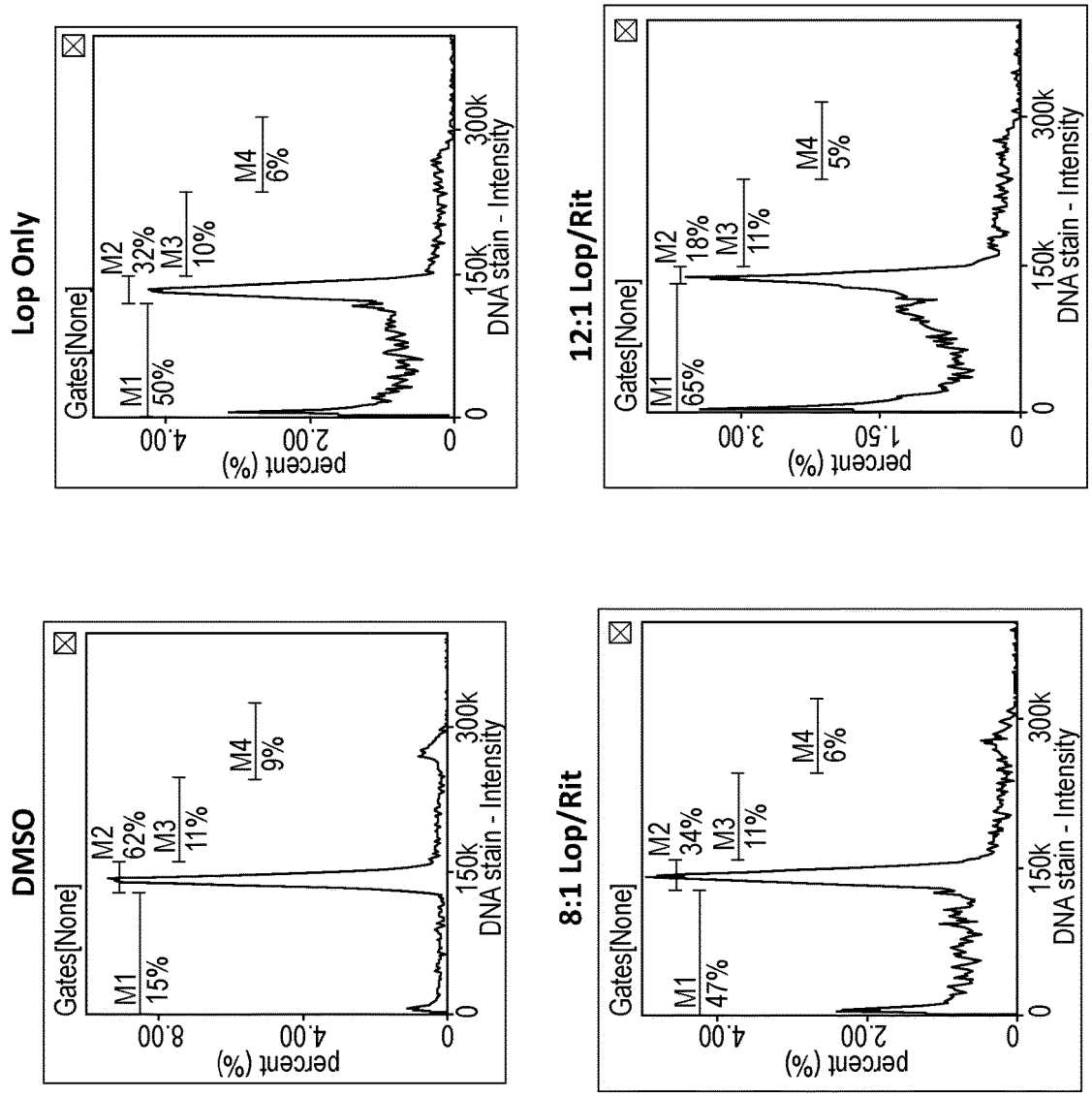

FIG. 3(A) represents data presented as the percentage of cells which are undergoing apoptotic DNA fragmentation (Sub G1) versus those which have intact 2N DNA (G1) following treatment with DMSO (control); 20 μM lopinavir alone; and lopinavir and ritonavir at 8:1 or 12:1 (w/w). The data illustrates that lopinavir:ritonavir in a ratio according to the invention (12:1) was significantly more effective for killing SiHa cells than lopinavir alone or the APIs at a ratio of 8:1 (w/w).

This illustrates that lopinavir and ritonavir, in ratios according to the invention, will have improved efficacy for treating HPV-related malignant disease and ICC.

FIG. 3(B) represents the cell cycle/DNA fragmentation profile (as Box and Whisker Plots) generated from the Image Cytometer and is included to illustrate the raw data from which FIG. 3(A) is derived. Similar profiles (not presented) were the basis for FIGS. 1, 2 and 4.

Example 4

Assessment of the effects of 10:1 and 12:1 w/w ratios of Lopinavir:Ritonavir at a total API concentration of 25 μM on HPV16 positive SNU17 cervical carcinoma cells SNU17 cells are HPV16 positive cervical cell carcinoma cell derived from a 40-year-old Mongolian women and were obtained from Creative Bioarray. The cell line is a further model for treating HPV-related malignant disease and Invasive cervical cancer (ICC).

4.1 METHODS

The methods described in 1.1 were followed except:

4.1.1: The cells were cultured in the T25 flasks for 4 days. The first two days followed standard culture conditions whereas for days 3 and 4 the cells were grown in growth medium without FCS.

4.1.2: Culture was continued for a further 3 days in RPMI growth medium containing 5% FCS and a total API concentration of 25 μM and with lopinavir and ritonavir present in the ratios discussed in the results section.

4.2 RESULTS

Figure 4:
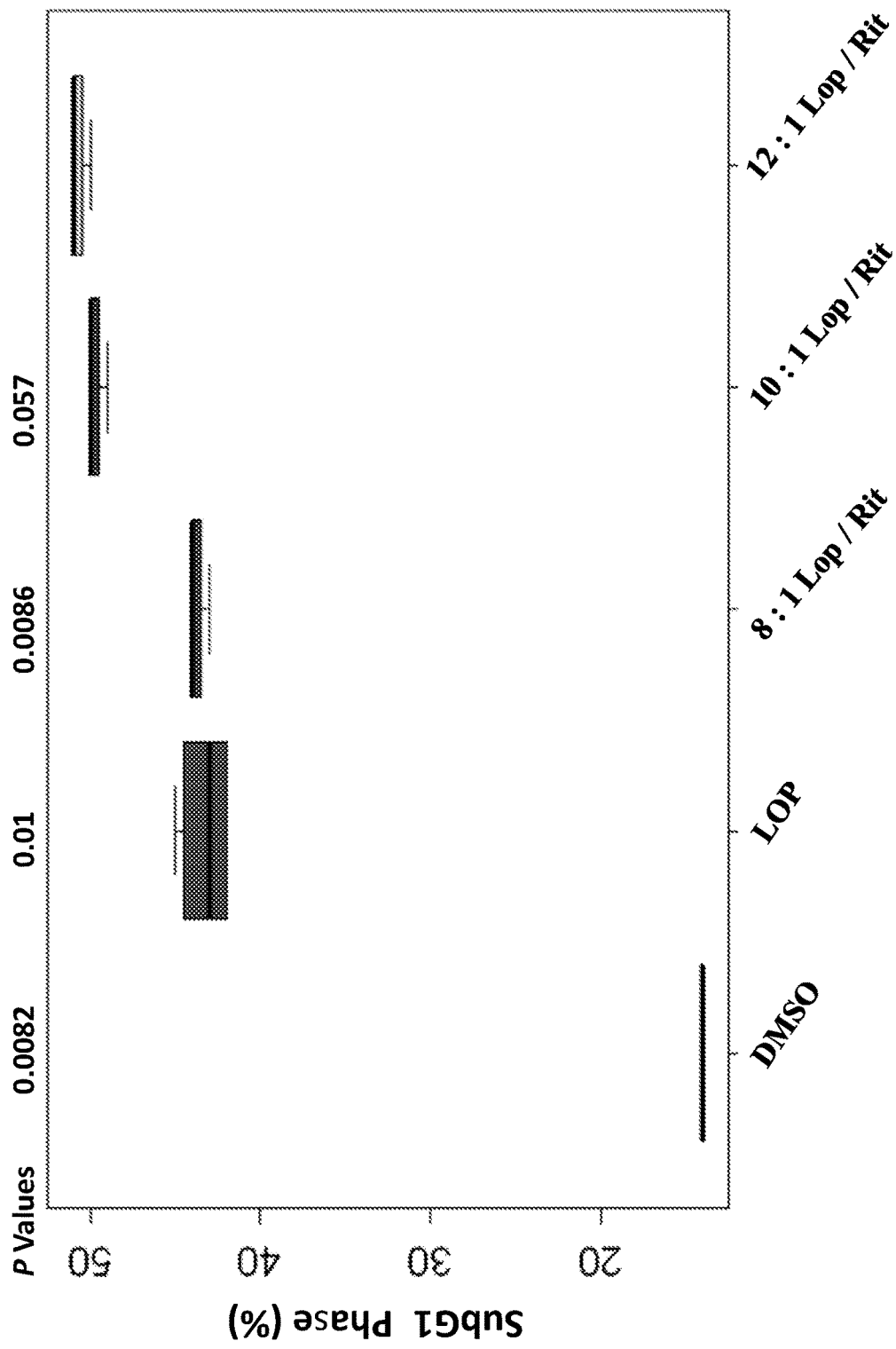
FIG. 4, is a bar chart illustrating the effects of 10:1 and 12:1 weight ratios of lopinavir:ritonavir on inducing apoptosis in HPV16+ve SNU17 cells as discussed in Example 4.

FIG. 4 represents data presented as the percentage of cells which are undergoing apoptotic DNA fragmentation (Sub G1) versus those which have intact 2N DNA (G1) following treatment with DMSO (control); 20 μM lopinavir alone; and lopinavir and ritonavir at 8:1, 10:1 or 12:1 (w/w). The data illustrates that lopinavir:ritonavir in ratios according to the invention (10:1 and 12:1 (w/w)) are significantly more effective for killing SNU17 cells than lopinavir alone or the APIs at a ratio of 8:1 (w/w).

Example 5

Assessment of the effects of small changes in w/w ratios (11-13.5) of Lop/Rit at a total API concentration of 20 μM on Hela cells Additional experiments were conducted to further evaluate the optimal ratio of lopinavir:ritonavir for use according to the invention.

5.1 METHODS

The methods described in Example 2 were followed.

5.2 RESULTS

Figure 5:
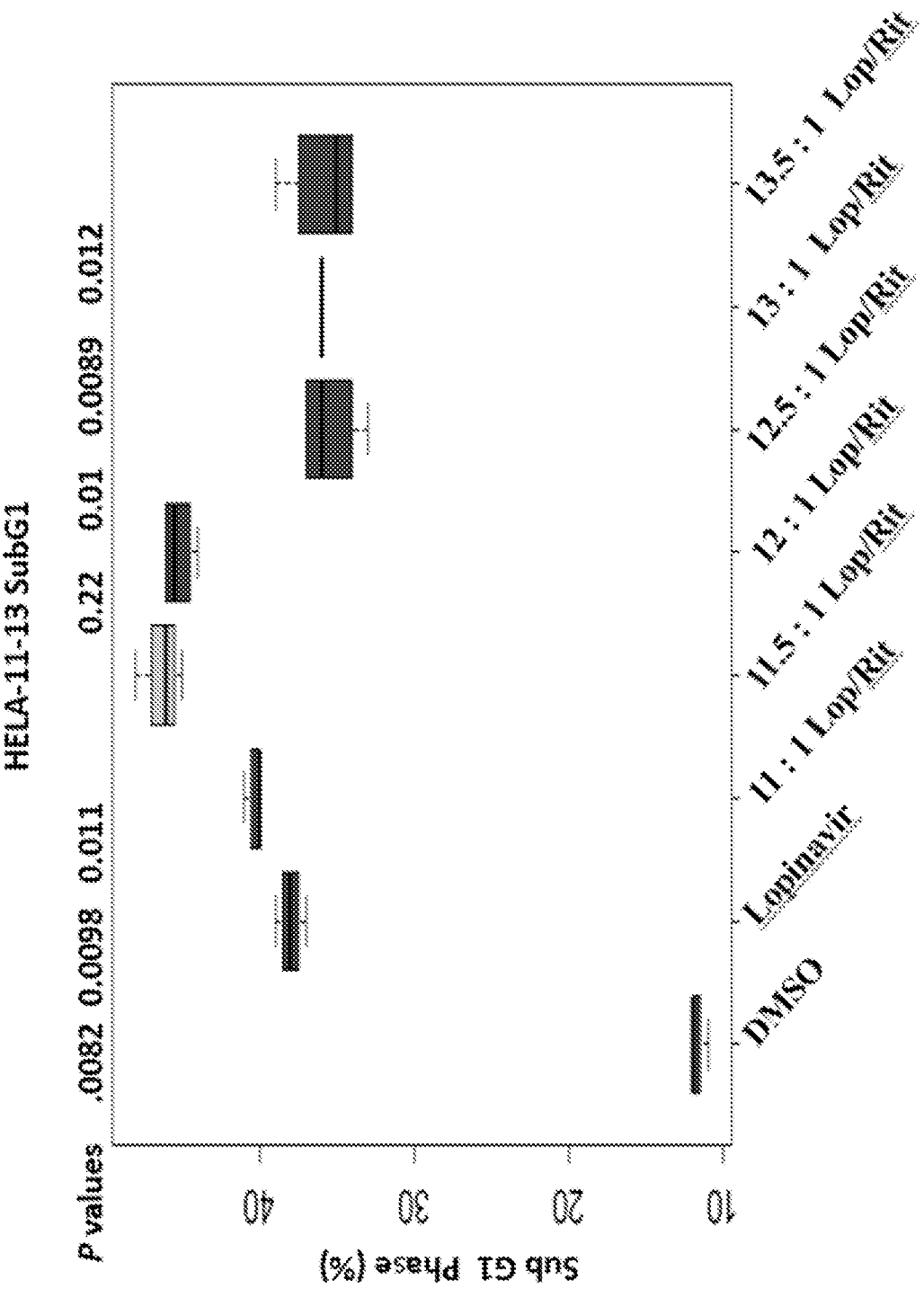
FIG. 5 represents: (A) a bar chart illustrating the effects of smaller changes in the w/w ratios of lopinavir:ritonavir between 11 and 13.5:1 on their ability to induce apoptosis in Hela cells and (B) illustrative cytometer results from which the data in the bar charts are based.
Figure 5:
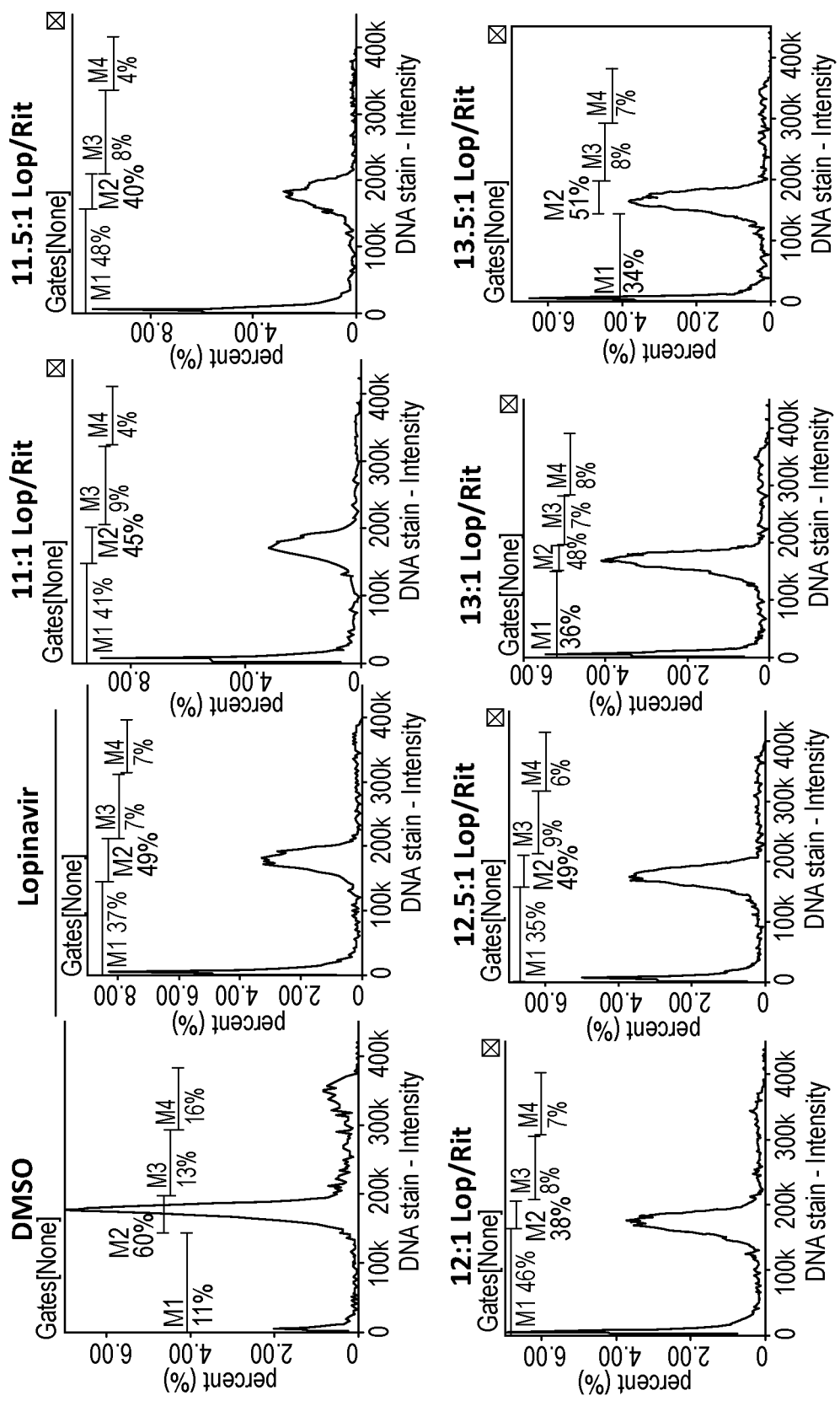

FIG. 5(A) represents data presented as the percentage of cells which are undergoing apoptotic DNA fragmentation (Sub G1) versus those which have intact 2N DNA (G1) following treatment with DMSO (control); 20 μM lopinavir alone; and lopinavir and ritonavir at 11:1, 11:5, 12:1, 12.5:1; 13:1 and 13:5 (w/w). The data illustrates that lopinavir:ritonavir in ratios according to the invention, and particularly at 11.5 and 12:1, were significantly more effective for killing HeLa cells than lopinavir alone.

This illustrates that lopinavir and ritonavir, in ratios according to the invention, will have improved efficacy for treating HPV-related malignant disease.

FIG. 5(B) represents the cell cycle/DNA fragmentation profile (as Box and Whisker Plots) generated from the Image Cytometer and is included to illustrate the raw data from which FIG. 5(A) is derived. Similar profiles (not presented) were the basis for FIGS. 1, 2 and 4.

Example 6

Assessment of the effects of small changes in w/w ratios (11-13.5) of Lop/Rit at a total API concentration of 20 μM on SIHA cells Further experiments were conducted to further evaluate the optimal ratio of lopinavir:ritonavir for use according to the invention.

6.1 METHODS

The methods described in Example 3 were followed.

6.2 RESULTS

Figure 6:
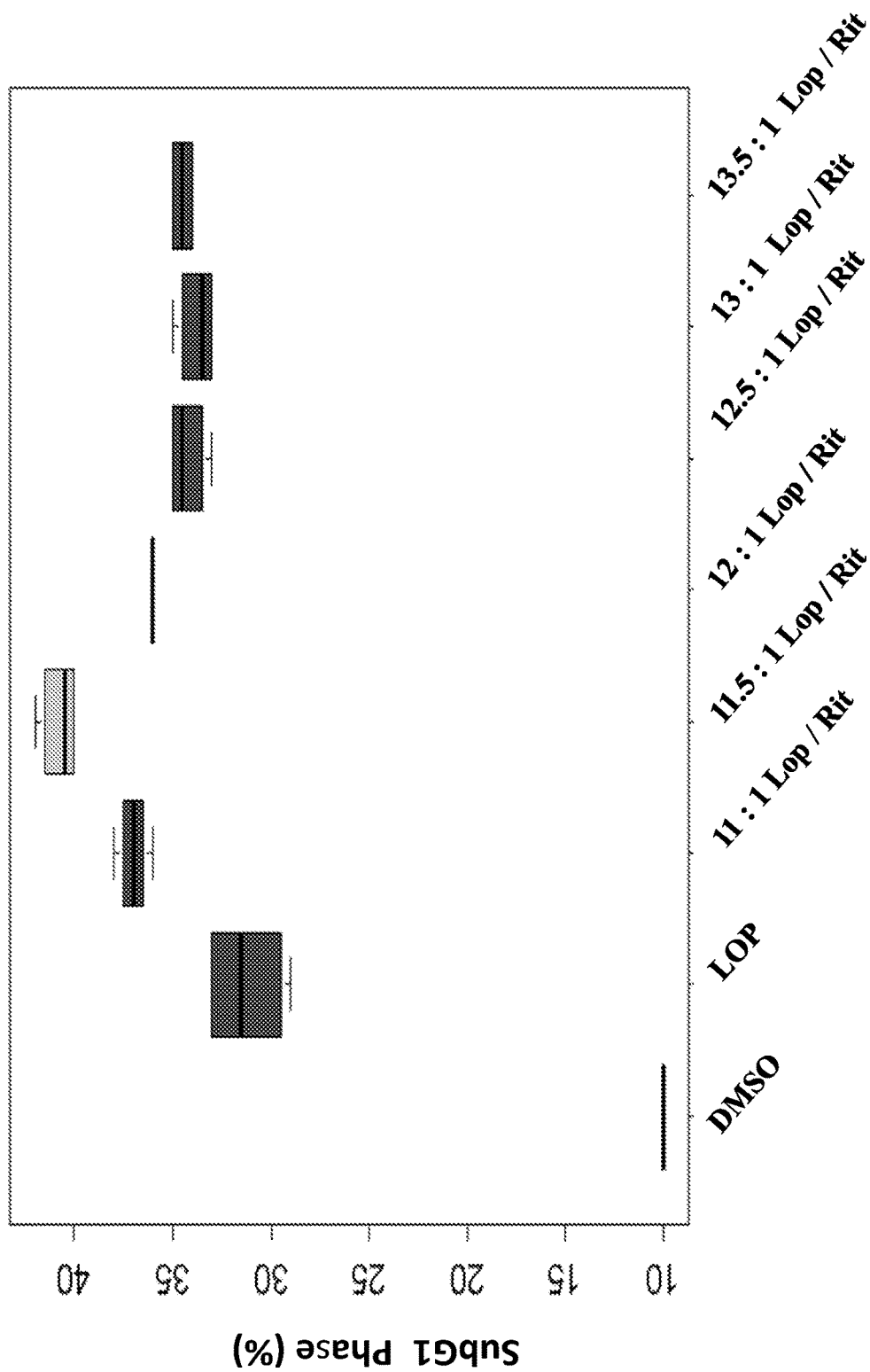
FIG. 6 is a bar chart illustrating the effects of smaller changes in the w/w ratios of lopinavir:ritonavir between 11 and 13.5:1 on their ability to induce apoptosis in SiHa cells

FIG. 6 represents data presented as the percentage of cells which are undergoing apoptotic DNA fragmentation (Sub G1) versus those which have intact 2 N DNA (G1) following treatment with DMSO (control); 20 µM lopinavir alone; and lopinavir and ritonavir at 11:1, 11:5, 12:1, 12.5:1; 13:1 and 13:5 (w/w). The data illustrates that lopinavir:ritonavir in a ratios according to the invention, and particularly at 11:1, 11.5 and 12:1, were significantly more effective for killing SiHa cells than lopinavir alone.

This illustrates that lopinavir and ritonavir, in ratios according to the invention, will have improved efficacy for treating HPV-related cervical malignant disease or ICC.

These data presented in Example 1-6 illustrate that lopinavir and ritonavir in ratios according to the invention have significantly greater effects on induced cell death than lopinavir alone or lopinavir and ritonavir in ratios that fall outside the range defined for the present invention. The fact that the preferred API ratios were efficacious in each of E6/E7 immortalised endocervical, HeLa, SiHa and SNU17 cells clearly demonstrate the usefulness of lopinavir and ritonavir, in the defined ratios, for treating HPV-related cervical pathologies.

These data presented in Example 1-6 illustrate that lopinavir and ritonavir in ratios according to the invention have significantly greater effects on induced cell death than lopinavir alone or lopinavir and ritonavir in ratios that fall outside the range defined for the present invention. The fact that the preferred API ratios were efficacious in each of E6/E7 immortalised endocervical, HeLa, SiHa and SNU17 cells clearly demonstrate the usefulness of lopinavir and ritonavir, in the defined ratios, for treating cervical pathologies and particularly HPV-related malignant disease.

Example 7

Preparation of Preferred Formulations

For all formulations present below, all materials used are pharmaceutical grade (either US Pharmacopeia or European Pharmacopeia) except for white ceresin wax, which is Japanese Pharmaceutical Excipient grade.

The manufacture of a vaginal dosage form exhibiting rheology suitable for syringe applicator vaginal dosing is described below in accordance with Tables 2-5.

i. Add into the mixer the following materials—3,4,5,6,7,8,9,1,10,11
ii. Exclude air from the interior of the vessel
iii. Heat to 70° C. while low shear mixing, to achieve a clear, transparent melt.
iv. Add into the mixer the following material—2
v. Exclude air from the interior of the vessel
vi. Mix via low shear, to finely disperse the HPMC within the melt
vii. Reduce the content temperature to 45° C. while low shear mixing
viii. Discharge to storage vessel and exclude air during storage.
ix. Pack composition into aluminium tubes, suitable for dispensing 1.0-5.0 g of composition. Aluminium tubes may contain a volume of 20-50 mls of composition.

TABLE 2

| # | Ingredient | Function(s) | % w/w |
|---|---|---|---|
| 1 | Oleic acid | Unsaturated free fatty acid | 62.823 |
| 2 | Hypromellose 2208 (4000 cps) | Muco-adhesive | 1.00 |
| 3 | Mono di glycerides (type 1) | Thickener | 5.00 |
| 4 | White ceresin wax | Thickener | 6.00 |
| 5 | Hydrogenated vegetable oil (type 1) | Thickener | 10.00 |
| 6 | Polyoxyl 100 stearate | Blending agent | 2.00 |
| 7 | Stearic acid | Stiffening agent | 4.50 |
| 8 | Glycerol monooleater | Blending agent | 3.00 |
| 9 | Butylatedhydroxytoluene | Antioxidant | 0.20 |
| 10 | Lopinavir | API | 5.000 |
| 11 | Ritonavir | API | 0.4775 |
| | TOTAL | | 100.000 |

TABLE 3

| # | Ingredient | Function(s) | % w/w |
|---|---|---|---|
| 1 | Oleic acid | Unsaturated free fatty acid | 57.345 |
| 2 | Hypromellose 2208 (4000 cps) | Muco-adhesive | 1.00 |
| 3 | Mono di glycerides (type 1) | Thickener | 5.00 |
| 4 | White ceresin wax | Thickener | 6.00 |
| 5 | Hydrogenated vegetable oil (type 1) | Thickener | 10.00 |
| 6 | Polyoxyl 100 stearate | Blending agent | 2.00 |
| 7 | Stearic acid | Stiffening agent | 4.50 |
| 8 | Glycerol monooleater | Blending agent | 3.00 |
| 9 | Butylatedhydroxytoluene | Antioxidant | 0.20 |
| 10 | Lopinavir | API | 10.000 |
| 11 | Ritonavir | API | 0.9550 |
| | TOTAL | | 100.000 |

TABLE 4

| # | Ingredient | Function(s) | % w/w |
|---|---|---|---|
| 1 | Oleic acid | Unsaturated free fatty acid | 61.800 |
| 2 | Hypromellose 2208 (4000 cps) | Muco-adhesive | 1.00 |
| 3 | Mono di glycerides (type 1) | Thickener | 5.00 |
| 4 | White ceresin wax | Thickener | 6.00 |
| 5 | Hydrogenated vegetable oil (type 1) | Thickener | 10.00 |
| 6 | Polyoxyl 100 stearate | Blending agent | 2.00 |
| 7 | Stearic acid | Stiffening agent | 4.50 |
| 8 | Glycerol monooleater | Blending agent | 3.00 |
| 9 | Butylatedhydroxytoluene | Antioxidant | 0.20 |
| 10 | Lopinavir | API | 6.000 |
| 11 | Ritonavir | API | 0.500 |
| | TOTAL | | 100.000 |

TABLE 5

| # | Ingredient | Function(s) | % w/w |
|---|---|---|---|
| 1 | Oleic acid | Unsaturated free fatty acid | 55.300 |
| 2 | Hypromellose 2208 (4000 cps) | Muco-adhesive | 1.00 |
| 3 | Mono di glycerides (type 1) | Thickener | 5.00 |
| 4 | White ceresin wax | Thickener | 6.00 |
| 5 | Hydrogenated vegetable oil (type 1) | Thickener | 10.00 |
| 6 | Polyoxyl 100 stearate | Blending agent | 2.00 |
| 7 | Stearic acid | Stiffening agent | 4.50 |

TABLE 5-continued

| # | Ingredient | Function(s) | % w/w |
|---|---|---|---|
| 8 | Glycerol monooleater | Blending agent | 3.00 |
| 9 | Butylatedhydroxytoluene | Antioxidant | 0.20 |
| 10 | Lopinavir | API | 12.000 |
| 11 | Ritonavir | API | 1.000 |
| | | TOTAL | 100.000 |

The manufacture of a placebo ointment suitable for syringe applicator vaginal dosing is described below in accordance with Table 6.
 i. Add into the mixer the following materials—3,4,5,6,7,8,9,1,
 ii. Exclude air from the interior of the vessel
 iii. Heat to 70° C. while low shear mixing, to achieve a clear, transparent melt.
 iv. Add into the mixer the following material—2
 v. Exclude air from the interior of the vessel
 vi. Mix via low shear, to finely disperse the HPMC within the melt
 vii. Reduce the content temperature to 45° C. while low shear mixing
 viii. Discharge to storage vessel and exclude air during storage.
 ix. Pack composition into aluminium tubes, suitable for dispensing 1.0-5.0 g of composition. Aluminium tubes may contain a volume of 20-50 mls of composition.

TABLE 6

| # | Ingredient | Function(s) | % w/w |
|---|---|---|---|
| 1 | Oleic acid ** | Unsaturated free fatty acid | 68.30 |
| 2 | Hypromellose 2208 (4000 cps) | Muco-adhesive | 1.00 |
| 3 | Mono di glycerides (type 1) | Thickener | 5.00 |
| 4 | White ceresin wax | Thickener | 6.00 |
| 5 | Hydrogenated vegetable oil (type 1) | Thickener | 10.00 |
| 6 | Polyoxyl 100 stearate | Blending agent | 2.00 |
| 7 | Stearic acid | Stiffening agent | 4.50 |
| 8 | Glycerol monooleate* | Blending agent | 3.00 |
| 9 | Butylatedhydroxytoluene | Antioxidant | 0.20 |
| | | TOTAL | 100.00 |

*Melt completely/mix source supply prior to dispensing
** N2 purge source supply after sampling
***Protect from UV light Example 8

A Preferred Dosing Regimen

Subjects were provided with aluminium tubes comprising the composition defined in Table 5.

Subjects were instructed to apply 2.5 g of the composition to the cervix, once a day and preferably in the evening. The aluminium tubes were adapted to load disposable syringes with 2.5 g of the composition. After use the syringes were disposed of. The aluminium tube may be used to load a syringe on subsequent days if the tube still contains sufficient composition.

Treatment may continue for 14-21 days as recommended by a physician. Treatment may then be stopped (and this halt may be timed to coincide with menses) for 1-14 days. During this time a clinical reassessment can be conducted; then, if necessary a further treatment cycle or cycles may be administered for a further 14-21 days per cycle. After each cycle a further clinical assessment can be made, and a decision made about whether subsequent treatment cycles are required.

Example 9

A Phase 1, Single Centre, Double Blind, Randomised, Parallel Group, Ascending Single and Multiple Dose, Safety and Tolerability, Pharmacokinetic (PK) and Pharmacodynamic (PD) Study of Preferred Formulations in Healthy Women Volunteers The compositions according to Tables 2 and 3 were investigated according to the clinical trial described below (and compared to the placebo of Table 6).
 9.1 Methods
 Study Objectives
 1. To evaluate the safety, PK and PD of compositions in healthy women volunteers after multiple doses of Formulations according to Tables 2 and 3.
 2. To observe the rates of side effects reported by women using the compositions compared to placebo.
 Investigational Plan/Study Design
 This study comprises two cohorts, both in healthy volunteers with no cervical pathology. There were 9 participants per Cohort, of whom 6 received active and 3 receive placebo. For all formulations tested, the amount of the composition administered per dose is 3 g. For composition of Table 3 this equates to 300 mg of lopinavir and 28.7 mg of ritonavir being administered to the patients per dose. For the composition of Table 2 this equates to 150 mg of lopinavir and 14.3 mg of ritonavir administered per dose.
 Cohort 1:
 Period 1: Single dose of composition of Table 2 or placebo followed by confinement. PK blood sampling during confinement.
 Period 2: 21 daily doses of composition of Table 2 or placebo followed by PK blood sampling.
 Cohort 2:
 Period 1: Single dose of composition of Table 3 or placebo followed by confinement. PK blood sampling during confinement.
 Period 2: 21 daily doses of composition of Table 3 or placebo followed by PK blood sampling.
 Participation Criteria
 Inclusion Criteria:
 a. Women, 20 to 45 years old, with an intact uterus and vagina.
 b. Generally, in good health with no clinically significant pulmonary, cardiac, gastroenterological, pancreatic, neurologic, renal, musculoskeletal, rheumatologic, metabolic, neoplastic, or endocrine disease.
 c. BMI of =>19 and <=30.0
 d. ECG and vital signs within normal ranges
 e. Agree to no Alcohol from 48 hours prior to dosing in period 1 until 7 days after receiving the final dose in period 2.
 f. Abstain from food or beverages containing grapefruit, starfruit, pomegranate, pineapple, or pomelo for the entire study
 g. Able and willing to abstain from sexual intercourse +/−6 hours around dosing within Periods 1 and 2
 h. Able and willing to use stringent methods of contraception after required abstinence period through to Day 29 (7 days after receiving the final dose in period 2), including the use of a non-latex condom (for partner protection) and a second acceptable contraception method; vasectomy, contraceptive pill, contraceptive implants or IUDs are allowed. (note: IUDs should have been inserted at least 1 month prior to enrolment and not because of the involvement in this study)

i. Agree to abstain from activities such as vaginal douching or insertion of any vaginal products other than the study drug for at least 48 hours prior to enrolment and throughout the study.

j. Negative Pap test at screening or within 3 years of enrolment and no history of cervical intraepithelial lesions within the previous 3 years k. Able and willing to return to the clinic for all study procedures.

l. Able and willing to provide informed consent.

Exclusion Criteria:

a. Women who are pregnant, plan to become pregnant in the next 3 months, or lactating females.

b. History of genital herpes with >3 outbreaks per year, or active non-HPV vaginal infection c. Positive result for Hep B, Hep C or HIV.

d. Have an active pelvic infection (positive urine screen for gonorrhoea or chlamydial infection, positive test and symptoms for bacterial vaginosis, candida vaginitis or trichomonal vaginitis)

e. Current or recent abnormal vaginal discharge and/or abnormal vaginal bleeding, within the 3 months prior to randomization as accessed by Investigator.

f. Had an abortion or miscarriage within the 3 months prior to randomization g. Currently taking any of the following medications: oral corticosteroids, inhaled salmeterol and fluticasone; immunomodulatory treatments, over the counter (OTC) intravaginal preparation, or any prescription that in the opinion of the Investigator could interfere with the interpretation of the results.

h. Currently taking any of the medications listed here- Alfuzosin, Amiodarone, dronedarone, Ranolazine, Fusidic Acid, Colchicine, Astemizole, terfenadine, Lurasidone, Pimozide, Quetiapine, Dihydroergotamine, ergonovine, ergotamine, methylergonovine, Cisapride, Lovastatin, simvastatin, Avanafil, Sildenafil, Vardenafil, Oral midazolam, triazolam, St. John's wort.

i. Recent history (within previous 3 months) of Stevens-Johnson syndrome, erythema multiforme, urticaria, angioedema, deep vein thrombosis, tinnitus, vertigo, blood glucose disorders, pancreatitis, haemophilia.

j. Hypersensitivity to any component of R131 vaginal ointment excipients k. Participation in any clinical study with an experimental medication or device within 30 days or 5 half-lives (whichever is longer) of enrolment.

l. Current alcohol or substance abuse as assessed by the Investigator.

m. An employee or first-degree family member of an employee, the Sponsor, the CRO or study site.

n. Not having a GP

Screening Evaluations:

The screening evaluations must have been made within 3 months of randomization into the study. Screening consisted of the following components:

Demographic/Medical History

A complete medical history was taken from each participant.

Physical Examination

The physical examination consisted of a review of body systems with height and weight (in indoor clothing).

Blood Tests

The following laboratory blood tests are performed:

Electrolytes (sodium and potassium), ALT, GGT, ALP, albumin, total protein, total bilirubin, urea, uric acid, serum creatinine, TFT, fasting lipids, amylase, glucose, and HbA1c Haemoglobin, red cell count, PCV, MCV, MCH, platelet count, white cell count, neutrophils, lymphocytes, monocytes, eosinophils and basophils. CD4/CD8 counts HIV and hepatitis B and C.

The measurement at screening serve as a baseline to monitor any abnormalities that may manifest as a result of dosing Other Tests Drugs of abuse testing were carried out on all participants as part of the screening procedures. A urine sample was required to test for cannabinoids (marijuana), amphetamines, benzodiazepines and opiates (i.e. morphine, heroin and codeine).

Urinalysis dipstick to check for protein, leucocytes, nitrites, pH, specific gravity, glucose, ketones, and blood.

Vaginal swabs for microbiology (gonorrhoea, Chlamydia, bacterial vaginosis, candida) and HPV genotyping Alcohol breath testing was carried out at the Clinical Site on the first night of each confinement period.

Serum HCG testing was carried out on all participants as part of the screening procedures and within 3 days before the 1st dose.

Vital Signs

Vital signs were recorded and consisted of blood pressure (supine and sitting), heart rate, temperature and respiratory rate. Participants' vital signs should be within the following limits:

Heart rate ≥60 or ≤99 beats/minute

Supine:

Systolic Blood Pressure ≥90 or ≤160 mm Hg; Diastolic Blood Pressure ≥50 or ≤90 mm Hg Sitting:

Systolic Blood Pressure ≥90 or ≤160 mm Hg; Diastolic Blood Pressure ≥50 or ≤90 mm Hg Temperature ≥36° C. or ≤37.7° C.

Respiratory Rate ≥12 or ≤20 breaths/minute

Summary of Study Activities/Schedule of Events

Informed consent was needed from each participant. Participants were screened to confirm study eligibility.

Randomisation

Participants were randomized following the Principal Investigator or their delegates documented acceptance of participants following review of completed screening procedures.

Study Confinement

Participants arrived at approximately 5 pm on Day 1 and Day 22. The duration of study confinement was approximately 27 hours. Participants were released from the clinical site once the 24-hour post dose assessments had been completed.

Dosing

Dosing began at approximately 8 pm on each day dosing was scheduled. Participants are instructed to insert the medication in private. Dosing applicators were returned to study staff and examined to ensure the full dose has been applied and for reconciliation of study drug.

Sample Collection

Vaginal swabs were self-administered by the participants.

PK Blood samples: blood samples (8 mL) were drawn through venous catheters and transferred into vacutainers containing sodium heparin as the anti-coagulant. The time of collection is recorded as the time the full 8 mL of blood was collected. The venous catheters were kept patent by flushing with 1.5 mL-2.0 mL of heparinized saline following each sample (0-24 hours). The sampling intervals were at: Day 1-2: 0, 1, 2, 4, 8, 12, 24 hours; Day 22-23: 0, 1, 2, 4, 8, 12, 24 hours. Samples were collected at their due time. Any deviation should have been noted.

Sample Processing and Storage

Plasma: Plasma was separated by centrifugation at 3500 rpm for 5 minutes at about 4° C. No aids for separation of plasma from red cells was used. The plasma sample is transferred with clean pipettes. The assay was determined using a validated Analytical method.

Each plasma sample was placed into a polypropylene storage tube with a screw cap. The plasma was stored frozen at - 60° C. or colder at the clinical site pending transfer to a Laboratory for assay.

End of Study

Within one week after the last study day, each participant was required to provide a blood sample for analysis. Any abnormalities as compared to initial screening were monitored and followed up until they return to normal.

Participants were assessed for the occurrence of adverse events from consent until the last study day in each cohort.

Vital signs (blood pressure, heart rate, respiratory rate and temperature) at last study visit.

Laboratory tests (haematology (CBC, CD4+/CD8+peripheral lymphocyte count, biochemistry (RFT, LFT, electrolytes, TFT, fasting lipids, HbA1c, amylase), Serum HCG Pregnancy and urinalysis (dipstick), at last study visit.

A follow-up phone call to each participant is made within 7 days (+2 days) of the end of the study to record any possible Adverse Events (AE) post study. Any events are recorded in source documentation.

All AE's were followed-up until resolution, or until the Investigator was of the opinion that follow-up was no longer required, or until 30 days from the last dose (as long as the Investigator was satisfied that follow-up is no longer required), whichever is earlier.

Adverse Events

During confinement the designated Supervisor for the study or a delegated representative must have been present at the study site throughout the study. Principal Investigator or at least one delegated Trial Physician was on call throughout the studies. On all study visits each participant was asked how they felt. This occured at each sampling point throughout the study. AE's were recorded in source documentation.

Each AE was classified by the Principal Investigator as serious adverse event (SAE) or non-serious. Non-serious adverse events were assessed as being mild, moderate, or severe to describe the maximum intensity of the AE. The Principal Investigator also provided the possible relationship between the AE and the study medication as highly probable, probable, possible, remotely or not ("no") related to the study medication.

The Principal Investigator should have stated if the cause of the AE is related to the concurrent non-investigational medication(s) if any are being taken, an underlying disease, a combination of these factors or is unknown.

9.2 Results

Safety Results:

109 adverse events in total reported by 18 participants, see Table 7.

1 event 'related' to study medication
6 events 'probably related' to study medication
82 events 'possibly related' to study medication
6 events 'probably not related' to study medication
14 events 'not related' to study medication
No SAEs Conclusion:

The formulations according to the invention are deemed to be well-tolerated since all AEs were either minor or not related to administration of study medication.

TABLE 7

Adverse event summary:

| AE | Composition of Table 2 (Cohort 1) | Composition of Table 6 (Placebo) | Composition of Table 3 (Cohort 2) |
|---|---|---|---|
| Vaginal discharge | 5 | 4 | 5 |
| Vaginal pruritis | 4 | 5 | 3 |
| Vulvovaginal discomfort | 3 | 5 | 2 |
| Vaginal odour | 1 | 2 | 2 |
| Oligomenorrhoea | 4 | 2 | 3 |
| Pelvic pain | 2 | 2 | 0 |
| Vulvovaginal burning sensation | 1 | 2 | 0 |
| Vulvovaginal pain | 0 | 1 | 0 |
| Dysuria | 0 | 1 | 0 |
| Abdominal pain | 5 | 3 | 2 |
| Nausea | 0 | 1 | 0 |
| Abdominal distension | 0 | 0 | 1 |
| Bacterial vaginosis | 2 | 4 | 3 |
| Vulvovaginal candidiasis | 4 | 4 | 1 |
| Rhinorrhoea | 1 | 1 | 0 |
| Nasopharyngitis | 0 | 0 | 1 |
| Headache | 2 | 0 | 0 |
| Insomnia | 0 | 0 | 1 |
| Catheter site pain | 1 | 1 | 1 |
| Dizziness | 1 | 0 | 0 |
| Drug hypersensitivity | 1 | 0 | 0 |
| Decreased appetite | 0 | 0 | 1 |

Pharmacokinetic Analyses:

Pharmacokinetic Parameters:

The area under the plasma drug concentration time curve (AUC), the peak plasma drug concentration (Cmax) and the time to maximum drug concentration (Tmax) were determined for lopinavir and ritonavir for each subject receiving active treatment.

The plasma drug concentration (C) versus the real sampling time (t) data were analysed by a "noncompartmental" method to obtain the pharmacokinetic parameters. Initially the plasma data in the post distribution phase of the plasma concentration-time plot were fitted using linear regression to:

$$ln\ C = ln\ Co - t.Kel$$

where Co is the zero-time intercept of the extrapolated terminal phase and Kel is the terminal elimination rate constant.

The area ($AUC_{0-t}$) from time zero to the last determined concentration-time point (t) in the post distribution phase was calculated using the trapezoidal rule.

Lopinavir and Ritonavir Concentration and Pharmacokinetic Parameters

The mean lopinavir and ritonavir plasma concentration-time data for each sampling time is listed in Tables 8 and 9. The pharmacokinetic parameters for lopinavir and ritonavir are summarised in Tables 10 and 11.

TABLE 8

Mean (±SD) Plasma Lopinavir and Ritonavir Concentration Data vs Sampling Times (Composition of Table 2) Vaginal Ointment)

| | Lopinavir | | | | Ritonavir | | | |
|---|---|---|---|---|---|---|---|---|
| | Test Treatment B: Single Dose 1 × 3 g of 150 mg Composition of Table 2 Vaginal Ointment (n = 6) | | Test Treatment B: Multiple Dose 21 × 3 g of 150 mg Composition of Table 2 Vaginal Ointment (n = 5) | | Test Treatment B: Single Dose 1 × 3 g of 150 mg Composition of Table 2 Vaginal Ointment (n = 6) | | Test Treatment B: Multiple Dose 21 × 3 g of 150 mg Composition of Table 2 Vaginal Ointment (n = 5) | |
| Sample time (hrs) | Concentration Mean value (pg/mL) | S.D | Concentration Mean value (pg/mL) | S.D | Concentration Mean value (pg/mL) | S.D | Concentration Mean value (pg/mL) | S.D |
| 0 | 0.0 | 0.0 | 115.1 | 64.3 | 0.0 | 0.0 | 3.7 | 8.2 |
| 1 | 28.9 | 35.9 | 115.8 | 50.1 | 2.7 | 6.5 | 0.0 | 0.0 |
| 2 | 49.6 | 44.0 | 169.6 | 76.4 | 3.0 | 7.4 | 3.9 | 8.6 |
| 4 | 94.3 | 79.7 | 194.1 | 77.5 | 35.8 | 66.4 | 12.5 | 11.7 |
| 8 | 103.7 | 60.3 | 170.4 | 43.4 | 9.4 | 14.6 | 9.9 | 9.0 |
| 12 | 132.1 | 78.2 | 168.2 | 51.2 | 11.8 | 13.7 | 6.9 | 9.5 |
| 24 | 150.8 | 63.0 | 178.3 | 64.4 | 0.0 | 0.0 | 10.1 | 14.0 |

TABLE 9

Mean (±SD) Plasma Lopinavir and Ritonavir Concentration Data vs Sampling Times (Composition of Table 3) Vaginal Ointment)

| | Lopinavir | | | | Ritonavir | | | |
|---|---|---|---|---|---|---|---|---|
| | Test Treatment A: Single Dose 1 × 3 g of 300 mg Composition of Table 3 Vaginal Ointment (n = 6) | | Test Treatment A: Multiple Dose 21 × 3 g of 300 mg Composition of Table 3 Vaginal Ointment (n = 5) | | Test Treatment A: Single Dose 1 × 3 g of 300 mg Composition of Table 3 Vaginal Ointment (n = 6) | | Test Treatment A: Multiple Dose 21 × 3 g of 300 mg Composition of Table 3 Vaginal Ointment (n = 5) | |
| Sample time (hrs) | Concentration Mean value (pg/mL) | S.D | Concentration Mean value (pg/mL) | S.D | Concentration Mean value (pg/mL) | S.D | Concentration Mean value (pg/mL) | S.D |
| 0 | 0.0 | 0.0 | 334.7 | 310.3 | 0.0 | 0.0 | 40.2 | 43.1 |
| 1 | 55.5 | 73.1 | 288.9 | 234.2 | 4.5 | 11.1 | 44.6 | 43.9 |
| 2 | 114.8 | 165.8 | 344.9 | 310.0 | 11.8 | 28.8 | 34.0 | 38.3 |
| 4 | 181.4 | 241.0 | 323.2 | 252.9 | 12.3 | 30.1 | 44.0 | 31.9 |
| 8 | 198.7 | 181.8 | 307.4 | 211.6 | 14.7 | 20.5 | 37.3 | 21.8 |
| 12 | 179.4 | 141.8 | 337.7 | 218.4 | 16.0 | 22.0 | 39.5 | 24.3 |
| 24 | 169.2 | 71.1 | 248.4 | 186.9 | 12.1 | 13.4 | 29.4 | 14.8 |

TABLE 10

Pharmacokinetic Parameters for Lopinavir

| Pharmacokinetic Parameters | Test Treatment B: Single Dose 1 × 3 g of 150 mg Composition of Table 2 Vaginal Ointment (n = 6) (mean ± S.D) (Range) | Test Treatment B: Multiple Dose 21 × 3 g of 150 mg Composition of Table 2 Vaginal Ointment (n = 5) (mean ± S.D) (Range) | Pharmacokinetic Parameters | Test Treatment A: Single Dose 1 × 3 g of 300 mg Composition of Table 3 Vaginal Ointment (n = 6) (mean ± S.D) (Range) | Test Treatment A: Single Dose 21 × 3 g of 300 mg Composition of Table 3 Vaginal Ointment (n = 6) (mean ± S.D) (Range) |
|---|---|---|---|---|---|
| $AUC_{0-t}$ (pg · hr/ml) | 1560.2 ± 989.7 (491.1-3206.0) | 2529.1 ± 840.3 (1478.7-3614.2) | $AUC_{0-t}$ (pg · hr/ml) | 4021.1 ± 3093.5 (1710.9-9944.3) | 7368.1 ± 4973.1 (2366.4-13858.2) |
| Cmax (pg/ml) | 181.8 ± 66.9 (72.0-269.2) | 228.1 ± 60.3 (168.2-320.3) | Cmax (pg/ml) | 254.7 ± 211.7 (97.8-670.2) | 396.3 ± 297.3 (130.2-840.7) |
| Tmax(hr) | 18.72 ± 8.67 (4.00-24.23) | 11.61 ± 11.36 (2.00-24.03) | Tmax(hr) | 16.03 ± 9.16 (4.00-24.12) | 11.61 ± 8.06 (2.00-24.03) |

TABLE 11

Pharmacokinetic Parameters for Ritonavir

| Pharmacokinetic Parameters | Test Treatment B: Single Dose 1 × 3 g of 150 mg Composition of Table 2 Vaginal Ointment (n = 6) (mean ± S.D) (Range) | Test Treatment B: Multiple Dose 21 × 3 g of 150 mg Composition of Table 2 Vaginal Ointment (n = 5) (mean ± S.D) (Range) |
|---|---|---|
| $AUC_{0-t}$ (pg · hr/ml) | 161.1 ± 254.9 (0.0-667.8) | 165.0 ± 158.3 (16.5-407.8) |
| Cmax (pg/ml) | 45.5 ± 61.7 (0.0-169.1) | 21.2 ± 5.1 (15.6-27.9) |
| Tmax(hr) | 5.33 ± 4.13 (0.00-12.00) | 8.82 ± 8.71 (4.00-24.08) |

| Pharmacokinetic Parameters | Test Treatment A: Single Dose 1 × 3 g of 300 mg Composition of Table 3 Vaginal Ointment (n = 6) (mean ± S.D) (Range) | Test Treatment A: Single Dose 21 × 3 g of 300 mg Composition of Table 3 Vaginal Ointment (n = 6) (mean ± S.D) (Range) |
|---|---|---|
| $AUC_{0-t}$ (pg · hr/ml) | 313.5 ± 447.6 (0.0-1156.4) | 890.0 ± 548.3 (420.6-1564.5) |
| Cmax (pg/ml) | 23.1 ± 27.2 (0.0-73.8) | 53.3 ± 35.3 (25.3-98.5) |
| Tmax(hr) | 10.02 ± 11.27 (0.00-24.12) | 5.20 ± 4.77 (1.00-12.02) |

Discussion of Results:

Cmax:

Following an oral dose of 400 mg lopinavir (as Kaletra 400 mg/100 mg tablets)* twice daily for 2 weeks, the mean Cmax for lopinavir was 12.3±5.4 µg/mL (SPMC Kaletra). Adjusting for dose comparison with a 300 mg dose administered topically in ointment form, the mean Cmax would be 9.23±4.1 µg/mL.

Following a topical dose of 300 mg lopinavir daily for 21 days as 2.5 g ointment containing 12% w/w lopinavir, the mean Cmax was 396.3±297.3 pg/mL.

The ratio of Cmax oral/Cmax topical is >23,000 indicating that less than 0.004% of the topical dose is available systemically.

AUC 0-t:

Following an oral dose of 400 mg lopinavir (as Kaletra 400 mg/100 mg tablets)* twice daily for 2 weeks, the AUC0-t for lopinavir was 113.2±60.5 µgh/mL (SPMC Kaletra). Adjusting for dose comparison with a 300 mg dose administered topically in ointment form, the AUC0-t would be 84.9±45.4 µgh/mL.

Following a topical dose of 300 mg lopinavir daily for 21 days as 2.5 g ointment containing 12% w/w lopinavir, the AUC0-t was 7368.1±4973.1 pg/mL.

The ratio of AUC oral/AUC topical is >11,500 indicating that less than 0.009% of the topical dose is available systemically.

Conclusion:

The combined Cmax and AUC data indicate that systemic absorption of lopinavir from topical administration of the ointment is negligible.

Example 10

A Phase 1b, Multicentre, Open Label, Study of the Efficacy, Safety and Tolerability of a Composition Comprising Ritonavir and Lopinavir in Women with Cytological Abnormalities of the Uterine Cervix 10.1 Composition Used The composition according to Table 5 was used in a Phase 1b trial except, rather than employing the methodology of Example 7, a cold process was employed as described below.

The manufacture of a vaginal dosage form exhibiting rheology suitable for syringe applicator vaginal dosing is described below in accordance with Table 5:-
  i. Into medicine mixer add 1, 9, 10, 11
  ii. Lower the lid and purge with nitrogen
  iii. Mix without heating for several hours until a clear, transparent solution is achieved
  iv. Raise the lid and add 7
  v. Lower the lid and purge with nitrogen
  vi. Mix without heating until a clear, transparent solution is achieved
  vii. Raise the lid and add 2, 3, 4, 5, 6, 8
  viii. Lower the lid and purge with nitrogen
  ix. Mix without heating for several hours
  x. Discharge the product into bulk storage vessel, awaiting packing into aluminium tubes 10.2 Methodology Study Objectives Efficacy Objectives Demonstrate histological clearance of cytological abnormalities following application of a composition according to the invention in women with high-grade or low-grade CIN (Cervical intra-epithelial neoplasia).

Demonstrate changes to colposcopic appearance of the uterine cervix following application of a composition according to the invention;

Assess changes in HPV status following application of a composition according to the invention.

Safety Objective

Assess the incidence of AEs following the application of a composition according to the invention.

Tolerability Objective

Assess the tolerability of a composition according to the invention, measured by compliance with dosing schedule of a composition according to the invention during 21 consecutive days of treatment for up to 3 treatment cycles.

Study Design:

This study is designed as a Phase 1b multicentre, open label study investigating the efficacy, safety and tolerability of a composition according to the invention in women with cytological abnormalities of the uterine cervix.

In this single arm study, participants are stratified according to their grade of cytological abnormality:

Biopsy proven high-grade cytological abnormalities of the uterine cervix defined as CIN 2 and above;

Low-grade cytological abnormalities of the uterine cervix defined as CIN 1/LSIL.

The composition according to the invention is self-applied to the vagina once a day for 21 consecutive days in up to 3 treatment cycles. Participants attend a clinic visit 7 days after administration of the final dose of investigational product. Participants complete a daily diary card and Vaginal Irritation Questionnaire to capture compliance with investigational product administration, AEs and changes to concomitant medication.

Participation in this study includes a screening visit, up to 3 treatment cycles and an end of study visit as follows:

Screening Visit: Day -28 to Day 0.

Treatment Cycle 1:

Day 1* to Day 21: Treatment Cycle 1—investigational product applied once daily for 21 days;

Day 8, 15, 22: telephone follow up; check AEs, conmeds, compliance, dosing issues;

Day 28: visual assessment of disease, if no disease detected#, treatment is stopped, and a biopsy is performed 6 weeks later (Day 70).

Treatment Cycle 2:

Day 29** to Day 49: Treatment Cycle 2—non-responders, identified at Day 28, will continue investigational application once daily for 21 days;

Day 36, 43, 50: telephone follow up; check AEs, conmeds, compliance, dosing issues;

Day 56: visual assessment of disease, if no disease detected#, treatment is stopped, and a biopsy is performed 6 weeks later (Day 98).

Treatment Cycle 3:

Day 57** to Day 77: Treatment Cycle 3 non-responders, identified at Day 56, can continue investigational application once daily for 21 days OR be referred to their primary physician;

Day 64, 71, 78: telephone follow up; check AEs, conmeds, compliance, dosing issues;

Day 84: visual assessment of disease and biopsy performed 6 weeks later (Day 126)

Post-treatment assessment visit (PTAV)/Early termination visit (ETV): Day 70, Day 98 or Day 126 depending on response.

*Day 1 commences at the end of a participant's menstrual cycle.

** Day 29 and 57 may be delayed to the end of the participants' menstrual cycle if required.

If absence of disease, defined as no colposcopic evidence of CIN, participants are considered responders. If disease is detected, defined as ongoing colposcopic evidence of CIN, participants are considered non-responders.

Participation Criteria

Inclusion Criteria:

To be eligible for study entry participants must satisfy all of the following criteria:

1. Provision of written informed consent prior to any study specific procedures;

2. Female participants aged 25-45 years inclusive at the time of screening visit;

3. Positive result for cervical high-risk HPV (types 16, 18 or 'other');

4. High-grade cytological abnormality of the uterine cervix defined as CIN 2 as proven by colposcopic biopsy collected at screening

OR low-grade cytological abnormality of the uterine cervix defined as CIN 1/LSIL, as demonstrated by colposcopic biopsy within 6 months prior to screening.

Participants will be stratified according to their grade of cytological abnormality;

5. Transformation zone needs to be fully visible;

6. Generally, in good health with no clinically significant disease as determined by the investigator;

7. Regular menstrual cycle with an approximate 28-day cycle

OR women who are amenorrhoeic due to effective contraception (such as Mirena, Jadelle, or continuous COC)

8. Agree to abstain from activities such as vaginal douching or insertion of any vaginal products other than the study drug for at least 48 hours prior to enrolment and throughout the study. Tampons may be used during the menstrual cycle only.

9. Women of childbearing potential (WOCBP) must use a highly effective form of birth control (confirmed by the Investigator). Rhythm methods will not be considered as highly effective methods of birth control. Highly effective forms of birth control include:

True sexual abstinence (defined as refraining from heterosexual intercourse for the duration of the study and a minimum of 30 days following the last dose of study drug);

Vasectomised partner (provided that the partner is the sole sexual partner of the female participant with childbearing potential and that the vasectomised partner has received medical assessment of the surgical success);

Oral or transdermal combined (oestrogen and progestogen containing) hormonal contraception associated with inhibition of ovulation;

Oral, injectable or implantable progestogen-only hormone contraception associated with inhibition of ovulation (Depo-Provera™, Implanon);

Any effective intrauterine device/levonorgestrel intrauterine system;

Female sterilisation by tubal occlusion;

Evra Patch™.

WOCBP must agree to use a highly effective method of birth control, as defined above, from enrolment, and at least 14 days prior to Day 1, throughout the study duration and within 30 days after the last dose of IMP.

WOCBP are defined as women who are neither permanently sterilised (hysterectomy, bilateral oophorectomy, or bilateral salpingectomy), nor who are postmenopausal. Women will be considered post-menopausal if they have been amenorrhoeic for 12 months or more without an alternative biological or medical cause e.g. contraceptive method such as Mirena.

10. Male partners of female participants must agree to use condoms during sexual intercourse from the first dose of investigational product until 30 days after the participants last dose to avoid potential transfer of investigational product.

11. Able and willing to abstain from sexual intercourse from 6 hours prior to dosing until 6 hours after dosing;

12. Ability and willingness to attend the necessary visits to the study centre;

13. Ability to comprehend all study related documentation, including written informed consent form, and complete all study-related tasks including daily diary;

14. Be willing and able to adhere to the prohibitions and restrictions specified in the protocol. Exclusion Criteria:

Participants are excluded from the study if one or more of the following criteria are applicable:

1. Any significant disease or disorder (e.g. cardiovascular, pulmonary, gastrointestinal, hepatic, renal, neurological, musculoskeletal, endocrine, metabolic, malignant, psychiatric, major physical impairment) which, in the opinion of the investigator, may either put the participant at risk because of participation in the study, or may influence the results of the study, or the participant's ability to participate in the study;

2. Any clinically significant abnormal findings in physical examination, vital signs, haematology, clinical chemistry, or urinalysis during screening and at baseline, which in the opinion of the investigator, may put the participant at risk because of her participation in the study, or may influence the results of the study, or the participant's ability to complete entire duration of the study;

3. Pregnant, breastfeeding, or lactating women (WOCBP must have a negative serum pregnancy test at screening and a negative urine pregnancy test at the start of each treatment period [i.e. Day 1, Day 28, Day 56]);

4. Women who plan to become pregnant in the next 6 months;

5. History of genital herpes with >3 outbreaks per year, or active non-HPV vaginal infection;

6. Active pelvic infection (positive for gonorrhoea or chlamydial infection, positive test for bacterial vaginosis, candida vaginitis or trichomonal vaginitis). Participants with positive results can be re tested once during screening;

7. Positive bimanual exam consistent with pelvic inflammatory disease;

8. Positive result for hepatitis B, hepatitis C or human immunodeficiency virus;

9. Current or recent abnormal vaginal discharge and/or abnormal vaginal bleeding, within the 3 months prior to Day 1 as assessed by the investigator;

10. Had an abortion or miscarriage or taken the morning-after pill within the 3 months prior to enrolment;

11. Currently taking immunosuppressants, intra-vaginal preparations, or any prescription that in the opinion of the investigator could be a potential safety issue or interfere with the interpretation of the results;

12. Previous exposure to lopinavir/ritonavir (within 3 months prior to screening), contraindication to the use of lopinavir/ritonavir or known allergy, hypersensitivity, or intolerance to any component of lopinavir/ritonavir ointment excipients;

13. Previous HPV vaccination;

14. Recent history (within 3 months prior to screening) of Stevens-Johnson syndrome, erythema multiforme, urticaria, angioedema, deep vein thrombosis, tinnitus, vertigo, blood glucose disorders, pancreatitis, haemophilia;

15. Receipt of any investigational product within 30 days or 5 half-lives prior to dosing;

16. Employees of the clinical study team or family members (first-degree relatives) of such individuals or anyone involved in the planning and/or conduct of the study. Clinical study team refers to employees directly involved in the study who have been delegated study-related tasks accordingly;

17. Participants who, in the opinion of the Investigator, do not understand the information and procedures of the study, or would not be compliant with them (in particular the study restrictions and risks involved).

Dosing Schedule:

Investigational product is administered every day for 21 days for up to 3 cycles as follows:

Cycle 1 (daily at 8pm from Day 1 to Day 21);
Cycle 2 (daily at 8pm from Day 29 to Day 49);
Cycle 3 (daily at 8pm from Day 57 to Day 77).

There is a 7-day treatment cessation in between cycles to allow for menstruation.

Investigational product is self-administered by participants at approximately 8 pm (±1 hour) each evening. Participants are provided dosing instructions and important application instructions.

Participants record details of investigational product application in a diary card each day to monitor compliance. Participants are also asked to note in their diary card if there is any waste/spillage.

Participants are required to bring their investigational product and diary card to each study site visit. The tubes are to be weighed prior to dispensing to the participant and again at each clinic visit to assess compliance.

There are no fasting requirements associated with the timing of application of investigational product.

Safety Assessments

The following safety assessments are performed at timepoints outlined in the Schedule of Events, see Table 12.

Medical History
Physical Examination
Vital Signs
Body Weight and Height
12-lead Electrocardiogram
Clinical Laboratory Safety Tests (Haematology, Biochemistry, Urinalysis, Vaginal Microbiology, Viral Serology, Drugs of Abuse Screen, Alcohol Screen, Pregnancy Screen)

Efficacy Assessments

The efficacy of the investigational product are assessed by improvements in the cytological abnormalities of the uterine cervix. Efficacy assessments are performed at timepoints outlined in the Schedule of Events, see Table 12.

Colposcopic visual assessment
Colposcopic Biopsy
Cytological Sampling
HPV Genotyping

TABLE 12

| | Screening | Treatment Cycle 1 (all participants) | | | | | Treatment Cycle 2 (Treatment Cycle 1 non-responders only) | | | | | Treatment Cycle 3 (Treatment Cycle 1 and 2 non-responders only) | | | | | Post-treatment assessment/Early Termination Visit |
|---|---|---|---|---|---|---|---|---|---|---|---|---|---|---|---|---|---|
| | | | | | | | Day | | | | | | | | | | |
| | −28 to 0 | 1 | 8 | 15 | 22 | 28 | 29 | 36 | 43 | 50 | 56 | 57 | 64 | 71 | 78 | 84 | 6 weeks after last dose of Composition |
| Attend study site | X | X | | | | X | | | | | X | | | | | X | X |
| Telephone Follow up | | | X | X | X | | | X | X | X | | | X | X | X | | |
| Informed consent | X | | | | | | | | | | | | | | | | |
| Inclusion/ exclusion criteria | X | X | | | | | | | | | | | | | | | |
| Demographics | X | | | | | | | | | | | | | | | | |
| Medication history | X | | | | | | | | | | | | | | | | |
| Physical examination | X | | | | | | | | | | | | | | | | X |

TABLE 12-continued

| | Screening | Treatment Cycle 1 (all participants) | | | | Treatment Cycle 2 (Treatment Cycle 1 non-responders only) | | | | | Treatment Cycle 3 (Treatment Cycle 1 and 2 non-responders only) | | | | | Post-treatment assessment/Early Termination Visit |
|---|---|---|---|---|---|---|---|---|---|---|---|---|---|---|---|---|
| | | Day | | | | | | | | | | | | | | |
| | −28 to 0 | 1 | 8 | 15 | 22 | 28 | 29 | 36 | 43 | 50 | 56 | 57 | 64 | 71 | 78 | 84 | 6 weeks after last dose of Composition |
| Vital signs | X | X | | | | X | | | | | X | | | | | X | X |
| Weight, height | X | | | | | | | | | | | | | | | | |
| 12-lead Safety ECG | X | | | | | | | | | | | | | | | | |
| Alcohol breath test | X | | | | | | | | | | | | | | | | |
| Drugs of abuse screen | X | X | | | | | | | | | | | | | | | |
| Concomitant medications | X | X | X | X | X | X | X | X | X | X | X | X | X | X | X | X | X |
| Adverse events | X | X | X | X | X | X | X | X | X | X | X | X | X | X | X | X | X |
| Haematology | X | | | | | X | | | | | X | | | | | X | X |
| Biochemistry | X | | | | | X | | | | | X | | | | | X | X |
| Serology | X | | | | | | | | | | | | | | | | |
| Urinalysis | X | | | | | X | | | | | X | | | | | X | X |
| Pregnancy Test | X | | | | | X | | | | | X | | | | | X | X |
| Vaginal microbiology | X | | | | | X | | | | | X | | | | | X | X |
| Vaginal pH | X | | | | | X | | | | | X | | | | | X | X |
| Papanicolaou smear | X | | | | | | | | | | | | | | | | X |
| HPV genotyping | X | | | | | | | | | | | | | | | | X |
| Colposcopy visual assessment | X | | | | | X | | | | | X | | | | | X | X |
| Colposcopic biopsy | X | | | | | | | | | | | | | | | | X |
| Investigational product dispensed | | X | | | | X | | | | | X | | | | | | |
| compound administration | | X | X | X | | | X | X | X | | | X | X | X | | | |
| Participant diary/VIQ completion | | X- | — | — | — | X | — | — | — | — | X | — | — | — | — | X | |
| Review participant diary card and questionnaire | | | | | | X | | | | | X | | | | | X | |
| Review investigational product | | | | | | X | | | | | X | | | | | X | |

10.3 Results

Preliminary results for a subject with CIN1 at screening (who received 21 days of composition, no missed doses):

(A) Subject had slight irritation and vaginal itchiness thought out the 21 days but this subsided.

(B) Subject had colposcopy visual assessment after 21 days and no lesions could be detected.

Plan: as the condition had regressed the clinical assess felt there was no need to continue to cycle 2. Subject will be followed with end of study appointment

The invention claimed is:

1. A pharmaceutical composition that is formulated for topical application comprising a therapeutically effective amount of lopinavir and ritonavir in a pharmaceutically acceptable vehicle and wherein the weight ratio (w/w) of lopinavir: ritonavir is from 11:1 to 16:1.

2. The composition according to claim 1 for use as a medicament for treating and/or inhibiting the development or progression of cervical cancers and benign proliferative disorders of the cervix.

3. The composition according to claim 1 wherein lopinavir and ritonavir are included in a weight ratio of about 12:1.

4. The composition according to claim 1 wherein the composition is formulated as an ointment, gel, paste, cream, lotion, ovule, soft capsule, suppository, pessary, or any combination thereof.

5. The composition according to claim 1 wherein the pharmaceutically acceptable vehicle is an ointment.

6. The composition according to claim 5 wherein the composition is an anhydrous composition for topical application comprising:

(a) Lopinavir and ritonavir in a weight ratio from 11:1 to 16:1; and (b) a hydrophilic muco-adhesive agent;

wherein upon topical administration of the anhydrous composition to a site of application the anhydrous composition transforms into a muco-adhesive composition.

7. The composition according to claim 6 wherein the muco-adhesive agent is hydroxypropylmethylcellulose.

8. The composition according to claim 6 comprising ritonavir, lopinavir, hydroxypropylmethylcellulose, oleic acid, stearic acid; and butylated hydroxytoluene.

9. The composition according to claim 5 wherein the composition comprises:
 (a) an unsaturated free fatty acid;
 (b) a stiffening agent; and
 (c) lopinavir and ritonavir in a weight ratio from 11:1 to 16:1;
 wherein the unsaturated free fatty acid is present at a level of at least 20% by weight of the total pharmaceutical composition weight and wherein the pharmaceutical composition is a semi-solid at room temperature.

10. A method of treating and/or inhibiting the development or progression of cervical cancers and benign proliferative disorders of the cervix in a subject in need of such treatment or inhibition comprising administering a therapeutically effective amount of a pharmaceutical composition according to claim 1 to said subject.

11. The method according to claim 10 wherein the cancer or disorder is caused or induced by a human papilloma virus (HPV).

12. A method of treating a patient having an HPV related dysplasia of the cervix comprising administering intravaginally to said patient a therapeutically effective dose of a pharmaceutical composition according to claim 1.

13. The method of claim 12, wherein the pharmaceutical composition reduces the severity of the HPV related dysplasia.

14. The method of claim 13, wherein the severity of the HPV related dysplasia is reduced from CIN3 to CIN2, from CIN3 to CIN1, from CIN3 to HPV negative, from CIN2 to CIN1, from CIN2 to HPV negative, or from CIN1 to HPV negative.

15. The method of claim 11, wherein the composition induces apoptosis of HPV infected cells.

16. The method of claim 10, wherein the patient has a cervical cytology of high grade squamous intraepithelial lesion (HSIL), atypical squamous cells of undetermined significance (ASCUS), or low grade squamous intraepithelial lesion (LSIL).

17. The method of claim 16, wherein the composition reduces the cervical cytology from HSIL to a normal cytology, from HSIL to ACSUS, from HSIL to LSIL, from ACSUS to a normal cytology, or from LSIL to a normal cytology.

18. A method of treating a Human Papilloma Virus (HPV) infection with or without attendant abnormal pathology, comprising administering an effective amount of the pharmaceutical composition of claim 1.

* * * * *